US008877471B2

(12) United States Patent
De Maria et al.

(10) Patent No.: US 8,877,471 B2
(45) Date of Patent: Nov. 4, 2014

(54) PHYTASE VARIANTS

(71) Applicant: Novozymes A/S, Bagsvaerd (DK)

(72) Inventors: Leonardo De Maria, Frederiksberg (DK); Carsten Andersen, Vaerloese (DK); Lars Kobberoee Skov, Ballerup (DK); Mikael Blom Soerensen, Frederiksberg (DK)

(73) Assignee: Novozymes A/S, Bagsvaerd (DE)

( * ) Notice: Subject to any disclaimer, the term of this patent is extended or adjusted under 35 U.S.C. 154(b) by 0 days.

(21) Appl. No.: 13/874,954

(22) Filed: May 1, 2013

(65) Prior Publication Data

US 2013/0224332 A1 Aug. 29, 2013

Related U.S. Application Data

(62) Division of application No. 12/294,526, filed as application No. PCT/DK2007/000135 on Mar. 19, 2007, now Pat. No. 8,460,656.

(60) Provisional application No. 60/794,757, filed on Apr. 25, 2006, provisional application No. 60/788,966, filed on Apr. 4, 2006.

(30) Foreign Application Priority Data

Apr. 4, 2006 (DK) .................................. 2006 00484
Apr. 25, 2006 (DK) .................................. 2006 00581

(51) Int. Cl.
*C12N 9/00* (2006.01)
*C12N 9/16* (2006.01)
*A23K 1/165* (2006.01)

(52) U.S. Cl.
CPC ................ *C12N 9/16* (2013.01); *A23K 1/1653* (2013.01)
USPC ........................................... 435/183

(58) Field of Classification Search
CPC ....................................................... C12N 9/00
USPC ....................................................... 435/183
See application file for complete search history.

(56) References Cited

U.S. PATENT DOCUMENTS

| 7,867,743 B2 | 1/2011 | Wik et al. |
| 8,143,045 B2 * | 3/2012 | Miasnikov et al. ........... 435/196 |
| 2008/0292753 A1 | 11/2008 | Wik et al. |

FOREIGN PATENT DOCUMENTS

| EP | 0699762 A2 | 3/1996 |
| EP | 0897985 A2 | 2/1999 |
| JP | 7-059562 A | 3/1995 |
| JP | 2005-137293 | 6/2005 |
| JP | 2006-136314 | 6/2006 |
| WO | 99/49022 A1 | 9/1999 |
| WO | 01/36607 A1 | 5/2001 |
| WO | 01/90333 A2 | 11/2001 |
| WO | 03/102174 A2 | 12/2003 |
| WO | 2004/015084 A2 | 2/2004 |
| WO | 2004/085638 A1 | 10/2004 |
| WO | 2006/037327 A2 | 4/2006 |
| WO | 2006/037328 A1 | 4/2006 |
| WO | 2006/038062 A2 | 4/2006 |
| WO | 2006/038128 A2 | 4/2006 |
| WO | 2006038128 * | 5/2006 |
| WO | 2006/063588 A1 | 6/2006 |
| WO | 2007/006953 A1 | 1/2007 |

OTHER PUBLICATIONS

Goodenough et al., Molecular Biotechnoly, vol. 4, No. 2, pp. 151-166 (1995).
Haefner et al., Appl. Microbiol. Biotechnol., vol. 68, No. 5, pp. 588-597 (2005).
Kim et al., Biotechnology Letters, vol. 28, No. 1, pp. 33-38 (2006).
Vieille et al., Microbiology and Molecular Biology Reviews, vol. 65, No. 1, pp. 1-43 (2001).
Zinin, EMBL Database, Accession No. AY390262 (2004).

* cited by examiner

*Primary Examiner* — Karen Carlson
(74) *Attorney, Agent, or Firm* — Elias Lambiris

(57) ABSTRACT

The present invention relates to a phytase which has at least 74% identity to a phytase derived from *Citrobacter braakii* and comprises at least one alteration as compared to this phytase. These phytase variants have amended, preferably improved, properties, such as thermostability, temperature profile, pH profile, specific activity, performance in animal feed, reduced protease sensitiliby, and/or an amended glycosylation pattern. The invention also relates to DNA encoding these phytases, methods of their production, as well as the use thereof, e.g. in animal feed and animal feed additives.

30 Claims, 4 Drawing Sheets

| Variant |
| --- |
| P229S |
| D112V |
| Q82R |
| Q274H |
| D112Y |
| F88Y |
| K46E |
| S233C |
| R288M |
| I384L |
| Q385R |
| Q274L |
| E307Y |
| T199I |
| Q82K |
| T203I |
| K46E/Q82H |
| Q82K/V105I |
| N148D/T362I |
| K46E/L414I |
| F88Y/Y136N |
| N95P/N96S |

Fig. 1

| |
|---|
| N95P/N96P |
| Q97T/T98G |
| Y177F/T199I |
| Q274L/Q370H |
| K46E/N96Y |
| N148D/L301S |
| E24D/R288M |
| E140V/A322V |
| K46E/S195T |
| E75K/N365D |
| T98P/S235A |
| L160F/L215F |
| Q274L/K395T |
| G67R/Q279E/N308T |
| K161N/P229S/R288M |
| D53N/D57Y/M152V |
| F122Y/S156T/P229S |
| E23K/K46E/Q82H |
| K46E/Q82H/Q385R |
| T203W/E204N/K205R |
| T203W/E204H/K205R |
| T203W/E204R/K205R |
| T203W/E204A/K205R |
| A22T/K151G/N308D |
| E23K/E75K/F88Y |
| M152K/N225D/L301S |
| S78T/Q274L/S408I |
| L176Q/T199I/T366S |
| K46E/V77I/T203S |
| K46R/T199I/D367N |
| G74R/E204G/R288M |
| A22T/T199I/S206T/T207A |

Fig. 1 (cont.)

| |
|---|
| Q82R/F88Y/L126I/I384L |
| K46E/Q82H/E168D/Q274L |
| Q82K/T154I/Q279E/N308T |
| Q82R/D112V/Q274H/T362A |
| E24D/E79V/N95D/K360N |
| E23K/M28L/A109T/T143P/I384L |
| D53N/D57Y/T199I/P229S/R288M |
| K46E/Q82H/N148D/T154I/T362I |
| D53N/D57Y/P229S/R288M/K358R |
| D53N/D57Y/T154I/P229S/R288M |
| Y136N/T199I/T203L/E204I/K205P |
| E23Q/S101F/Q274L/I384M/K391N |
| K46E/Q82H/N95D/D112V/K142R/D383V |
| D53N/D57Y/M152V/P229S/R288M/A393P |
| D53K/D57Y/M152V/P229S/R288M/A393P |
| D53N/D57Y/F88Y/M152V/P229S/Q279E/N308T |
| D53N/D57Y/M152V/E204V/P229S/R288M/A393P |
| D53N/D57Y/M152V/T154I/P229S/R288M/A393P |
| D53N/D57Y/Q82H/G103E/M152V/P229S/R288M/A393P |
| K46E/D53N/D57Y/T143I/M152V/L176V/P229S/R288M/A393P |
| Q82K/F88Y/N96P/Q97T/T98G/V105I/Q274H/Q279E/A393P |
| Q82R/F88Y/N95P/N96P/Q97T/Q279E/I384L/P386Q/A393P |
| D53N/D57Y/E75V/M152V/A170T/P229S/R288M/Q385R/A393P |
| Q82K/F88Y/N96P/T98G/Y136N/M152V/Y177F/T362I/I384F/A393P/D397N |
| D53N/D57Y/F88Y/N95P/N96P/V105I/D112V/Y136N/N148D/N164D/Q274H/T362I/I384L/A393P |
| D53N/D57Y/Q82K/F88Y/N95P/P102L/V105I/Y136N/N148D/Y177F/Q274H/Q279E/T362I/A393P |
| D53N/D57Y/Q82K/F88Y/N96P/T98G/V105I/D112V/Y177F/Q274L/G343A/T362I/I384L/A393P |

Fig. 1 (cont.)

```
SEQ2         1                             EEQNGMKLERVVIVSRHGVRAPTKFTPI      28
                                           ||.||||||||||||||||||||||||
SEQ9         1 MSTFIIRLLFFSLLCGSFSIHAEEPNGMKLERVVIVSRHGVRAPTKFTPI           50

SEQ2        29 MKNVTPDQWPQWDVPLGWLTPRGGELVSELGQYQRLWFTSKGLLNNQTCP           78
               ||:|||||||||||||||||||||||||||||||||||||||||||||||
SEQ9        51 MKDVTPDQWPQWDVPLGWLTPRGGELVSELGQYQRLWFTSKGLLNNQTCP          100

SEQ2        79 SPGQVAVIADTDQRTRKTGEAFLAGLAPKCQIQVHYQKDEEKNDPLFNPV          128
               |||||||||||||||||||||||||||||||||||||||||.|||||||
SEQ9       101 SPGQVAVIADTDQRTRKTGEAFLAGLAPKCQIQVHYQKDEEKTDPLFNPV          150

SEQ2       129 KMGKCSFNTLQVKNAILERAGGNIELYTQRYQSSFRTLENVLNFSQSETC          178
               |||.||||||:|||||||||||||||||||||||||||||||||||||||
SEQ9       151 KMGTCSFNTLKVKNAILERAGGNIELYTQRYQSSFRTLENVLNFSQSETC          200

SEQ2       179 KTTEKSTKCTLPEALPSELKVTPDNVSLPGAWSLSSTLTEIFLLQEAQGM          228
               |||||||||||||||||||||||||||||||||||||||||||||||||
SEQ9       201 KTTEKSTKCTLPEALPSELKVTPDNVSLPGAWSLSSTLTEIFLLQEAQGM          250

SEQ2       229 PQVAWGRITGEKEWRDLLSLHNAQFDLLQRTPEVARSRATPLLDMIDTAL          278
               |||||||||||||||||||||||||||||||||||||||||||||||||
SEQ9       251 PQVAWGRITGEKEWRDLLSLHNAQFDLLQRTPEVARSRATPLLDMIDTAL          300

SEQ2       279 LTNGTTENRYGIKLPVSLLFIAGHDTNLANLSGALDLNWSLPGQPDNTPP          328
               |||||||||||||||||||||||||||||||||||||||||||||||||
SEQ9       301 LTNGTTENRYGIKLPVSLLFIAGHDTNLANLSGALDLNWSLPGQPDNTPP          350

SEQ2       329 GGELVFEKWKRTSDNTDWVQVSFVYQTLRDMRDIQPLSLEKPAGKVDLKL          378
               |||||||||||||||||||||||||||||||||||||||||||||||||
SEQ9       351 GGELVFEKWKRTSDNTDWVQVSFVYQTLRDMRDIQPLSLEKPAGKVDLKL          400

SEQ2       379 IACEEKNSQGMCSLKSFSRLIKEIRVPECAVTE         411
               ||||||||||||||||||||||||||||||||
SEQ9       401 IACEEKNSQGMCSLKSFSRLIKEIRVPECAVTE         433
```

PHYTASE VARIANTS

CROSS-REFERENCE TO RELATED APPLICATIONS

This application is a divisional of U.S. application Ser. no. 12/294,526 filed on Nov. 5, 2008, now U.S. Pat. No. 8,460,656, which is a 35 U.S.C. 371 national application of PCT/DK2007/000135 filed Mar. 19, 2007, which claims priority or the benefit under 35 U.S.C. 119 of Danish application nos. PA 2006 00484 and PA 2006 00581 filed Apr. 4, 2006 and Apr. 25, 2006, respectively, and U.S. provisional application nos. 60/788,966 and 60/794,757 filed Apr. 4, 2006 and Apr. 25, 2006, respectively, the contents of which are fully incorporated herein by reference.

REFERENCE TO SEQUENCE LISTING

This application contains a Sequence Listing in computer readable form. The computer readable form is incorporated herein by reference.

BACKGROUND OF THE INVENTION

1. Field of the Invention

The present invention relates to a phytase which has at least 74% identity to a phytase derived from *Citrobacter braakii* ATCC 51113 and comprises at least one alteration as compared to this phytase (i.e., is a variant thereof). The invention also relates to DNA encoding these phytases, methods of their production, as well as the use thereof, e.g. in animal feed and animal feed additives. The mature part of the *Citrobacter braakii* ATCC 51113 phytase is included in the sequence listing as SEQ ID NO: 2.

2. Background Art

The sequence of the phyA gene from *Citrobacter freundii* has been submitted by Zinin et al to the EMBL/GenBank/DDBJ databases with accession no. AY390262. The corresponding phytase amino acid sequence is found in the Uni-Prot/TrEMBL databases with accession no. Q676V7. The expected mature part of Q676V7 is included in the present sequence listing as SEQ ID NO: 4.

WO 2004/085638 discloses, as SEQ ID NO: 7, the amino acid sequence of a phytase from *Citrobacter braakii* YH-15, deposited as KCCM 10427. The mature part of this amino acid sequence is included herein as SEQ ID NO: 3. This sequence is also found in the database Geneseqp with accession no. ADU50737.

WO 2006/037328 discloses the wildtype phytase of *Citrobacter braakii* ATCC 51113 (i.e., SEQ ID NO: 2 herein), as well as a variant thereof, which is also included in the present sequence listing, viz. as SEQ ID NO: 6.

WO 2006/038062 and WO 2006/038128 both disclose the amino acid sequence of the phytase gene of *Citrobacter freundii* P3-42, deposited under accession number NCIMB 41247. This amino acid sequence is included herein as SEQ ID NO: 9.

It is an object of the invention to provide phytases of amended, preferably, improved properties. Non-limiting examples of such properties are: Thermostability, temperature profile pH profile, specific activity, performance in animal feed, protease-sensibility, and/or glycosylation pattern.

SUMMARY OF THE INVENTION

The present invention relates to a phytase which has at least 74% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411; with the proviso that the phytase is not SEQ ID NO: 3, not SEQ ID NO: 4, and not SEQ ID NO: 6.

The invention also relates to a phytase which has at least 74% identity to SEQ ID NO: 2 and which comprises at least one of the following alterations: 1H,K,R, 60P, 105E, 106A,G, 155F, 157F, 173P, 175L, 188P, 205P, 215M, 231P, 254Y, 280P, 330D, and/or 371P; with the proviso that the phytase is not SEQ ID NO: 3, not SEQ ID NO: 4, not SEQ ID NO: 6, and not SEQ ID NO: 9 and the variants thereof listed in FIG. 1.

The invention also relates to DNA encoding these phytases, methods of their production, as well as the use thereof, e.g. in animal feed and animal feed additives.

BRIEF DESCRIPTION OF THE DRAWINGS

FIG. 1 corresponds to Table 2 of WO 2006/038062 and discloses a number of variants of the *Citrobacter freundii* NCIMB 41247 phytase which has the amino acid sequence of SEQ ID NO: 9; and FIG. 2 is an alignment of the phytases of SEQ ID NO: 2 and 9.

The position numbers in FIG. 1 refer to the numbering of SEQ ID NO: 9. The corresponding SEQ ID NO: 2 positions can be found by deduction of 22 (e.g., variant P229S of FIG. 1 means variant P207S using the numbering of the present application).

DETAILED DESCRIPTION OF THE INVENTION

In a first aspect, the present invention relates to a phytase which has at least 74% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411; with the proviso that the phytase is not SEQ ID NO: 3, not SEQ ID NO: 4, and not SEQ ID NO: 6.

The percentage of identity is determined as described in the section "Phytase Polypeptides, Percentage of Identity".

The position numbers refer to the position numbering of SEQ ID NO: 2, as described in the section "Position Numbering." Positions corresponding to these SEQ ID NO: 2 position numbers in other phytases are determined as described in the section "Identifying Corresponding Position Numbers."

The phytase of the invention is a variant of the phytase of SEQ ID NO: 2, viz. it is not identical to SEQ ID NO: 2, as it comprises at least one alteration as compared to SEQ ID NO: 2.

In a particular embodiment, the phytase of the invention comprises at least one alteration as compared to SEQ ID NO: 2 in at least one position selected from the following: 1, 2, 3, 4, 5, 31, 46, 52, 53, 55, 57, 59, 76, 82, 99, 100, 107, 109, 111, 114, 115, 116, 117, 118, 119, 120, 121, 122, 123, 124, 137, 141, 161, 162, 164, 167, 179, 180, 181, 182, 183, 184, 185, 186, 196, 199, 200, 202, 218, 223, 241, 273, 276, 285, 286, 299, 314, 331, 339, 362, 379, 385, 406, 410, and 411.

In another particular embodiment the phytase of the invention is not SEQ ID NO: 9.

In a still further particular embodiment, the phytase of the invention is not the variants of SEQ ID NO: 9 listed in FIG. 1.

In a preferred embodiment, the phytase of the invention comprises at least one of the following alterations: 1*, 2*, 3*, 4P, 5P, 31C,T, 41P, 46C,D,E, 52C,E, 53V,Q, 55D,I, 57Y, 59C, 74A, 76G, 82E, 84Y, 91C,P, 99C, 100C, 104A, 105F, 107D, E,G, 109A,G, 111P, 114H,N,T, 115Q, 116A,E,P,T,Q, 117D, E,K 118I,L,M,T, 119G,K,R,S, 120K,S,T,Q, 121A,D,M,P,T, V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 331K, 339D, 351Y, 355P, 362K,R, 379K,R, 385D, 406A, 409D,E, 410D,E, and/or 411R,K.

The nomenclature used herein for alterations is described in detail in the section "Alterations, such as Substitutions, Deletions, Insertions."

Preferably the phytase of the invention comprises at least one of the following alterations: 1*, 2*, 3*, 4P, 5P, 31C, 46E, 52C,E, 53V, 55D, 57Y, 59C, 76G, 82E, 99C, 100C, 107D,E, G, 109A, 111P, 114T, 115Q, 116AT, 117D, 118T, 119K,R,S, 120S, 121D,P,T,122D, 123P, 124L, 137P, 141C, 161P, 162C, 164E, 167Q, 179K, 180E,T, 181D,K, 182H,K,Q, 183L,V,Q, 184*, 185*, 186*, 196Q, 199C, 200K, 202N, 218Q, 223E, 241Q, 273L, 276K,R, 285G,R, 286Q, 299L, 314G,N, 331K, 339D, 362K,R, 379K,R, 385D, 406A, 410D,E, and/or 411R, K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24).

In another preferred embodiment, the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24).

The invention also relates to a phytase which has at least 74% identity to SEQ ID NO: 2 and which comprises at least one of the following alterations: 1H,K,R, 60P, 105E, 106A,G, 155F, 157F, 173P, 175L, 188P, 205P, 215M, 231P, 254Y, 280P, 330D, and/or 371P; with the proviso that the phytase is not SEQ ID NO: 3, not SEQ ID NO: 4, not SEQ ID NO: 6, and not SEQ ID NO: 9 and the variants thereof listed in FIG. 1. In a preferred embodiment the phytase comprises the alteration 1K. In additional preferred embodiments, the phytase comprises the following combinations of alterations: 280P/282P/ 283P, 155F/254Y, and/or 155F/157F/254Y.

Preferred phytases of the invention comprise an alteration selected from the following: 52C, 141C, 162C, 31C, 52C, 99C, 59C, 100C, 141C/199C, 4P, 5P, 111P, 137P, 161P, 52E, 57Y, 76G, 107D, 107G, 109A, 1*, 1*/2*, 1*/2*/3*, 121T, 273L, 285G, 286Q, 299L, 362K, 331K/55D, 107E, 46E, 82E, 119R, 119K, 164E, 223E, 276K, 276R, 362R, 379R, 379K, 385D, 410D, 410E, 411R, 411K, 53V, 121D, 167Q, 196Q, 200K, 202N, 218Q, 241Q, 285N, 314N, 314G, 406A, 179K/ 180E/181K/182H/183Q/184*/185*/186*, 179K/180E/ 181K/182Q/183Q/184*/185*/186*, 179K/180E/181K/ 182K/183V/184*/185*/186*, 179K/180T/181D/182K/ 183L/184*/185*/186*, 111P/241Q, 1K, 114T/115Q/116A/ 117D/118T/119S/120S/121P/122D/123P/124L, and 114T/ 115Q/116T/117D/118T/119S/120S/121P/122D/123P/124L.

The phytase of the invention may be a variant of any wildtype or variant phytase. In particular embodiments, it is a variant of the phytase of SEQ ID NO: 2, SEQ ID NO: 3, SEQ ID NO: 4, SEQ ID NO: 6, SEQ ID NO: 9, or a variant of any one of the phytase variants related to SEQ ID NO: 9 and listed in FIG. 1.

The phytase of the invention may furthermore comprise an alteration (substitution) or a combination of alterations (substitutions) selected from amongst the alterations (substitutions) and combinations of alterations (substitutions) listed in each row of FIG. 1.

Particularly preferred variants of the phytase of SEQ ID NO: 2 are the following: R339D, N4P, G5P, Q111P, E1*, E1*/E2*, E1*/E2*/Q3*, M273L, and N286K; as well as any combination thereof; as well as the corresponding variants of SEQ ID NO: 3, 4 and 6.

Particularly preferred phytases of the invention comprise at least one of the following alterations: 339D, 4P, 5P, 111P, 1*, 1*/2*, 1*/2*/3*, 273L, and/or 286K.

The invention also relates to a phytase which has at least 74% identity to SEQ ID NO: 2 and which comprises at least one of the following alterations:

(i) 141C/199C, 91C/46C, 52C/99C, 31C/176C, 31C/177C, 59C/100C, and/or 162C/247C;
(ii) 41P, 91P, 136P, 137P, 154P, 161P, 355P, 111P, 240P, 282P, 283P, 284P, 289P, 4P, and/or 5P;
(iii) 52E, 55I, 57Y, 104A/105F, 107D,G, 109A,G, 76G, 84Y, 121T, 362K, 273L,Q, 285G,R, 286K,Q, 294T, 299L, 331K/55D, and/or 351Y;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) 119R,K, and/or 411R,K;
(vii) 107E, and/or 164E,D;
(viii) 362R,K, 276R,K, 379R,K, 409D,E, 223E, 385D, 46D, E, 410D,E, and/or 82E;
(ix) 218Q, 324N, 200R,K, 121D, 196Q, 202N, 406A, 167Q, 53V,Q, 241Q, 314N,G, 239Q, and/or 285N;
(x) 114H/115Q/116E/117K/118M/119G/120T/121M/122D/ 123P/124T, 114H/115Q/116Q/117D/118I/119K/120Q/ 121V/122D/123S/124L, 114H/115Q/116P/117E/118I/ 119G/120K/121M/122D/123P/124V, 114T/115Q/116A/ 117 D/118T/119S/120S/121P/122D/123P/124 L, 114H/ 115Q/116Q/117D/118I/119K/120Q/121A/122D/123P/ 124L, 114T/115Q/116T/117D/118T/119S/120S/121P/ 122D/123P/124L, or 114N/115Q/116N117D/118L/119K/ 120K/121T/122D/123P/124L;
(xi) 31T, 74A, 171T, 203T, 281H, 316D, and/or 308A; and/or
(xii) 339D.

Strategy for Preparing Variants

The structure of the *C. braakii* ATCC 51113 phytase was built by homology modelling, using as a template the structure of the *E. coli* AppA phytase (Protein Data Bank id.: 1DKO; Lim et al, Nat. Struct. Biol. (2000), vol. 2, pp. 108-113).

The structure was subjected to molecular dynamics (MD) simulations and electrostatic calculations. Positions for putative disulfide bridges and prolines were also identified, as well as other positions of potential importance as regards the various desirable enzymatic properties. Finally, putative glycosylation sites (stretches of NXT or NXS) were identified.

All these suggestions were evaluated within the framework of the modelled structure and the simulation results, for the thermostability property with particular emphasis at the high temperature end.

The corresponding phytase variants were prepared by methods known in the art and tested as described in the experimental part.

Phytase Polypeptides, Percentage of Identity

In the present context a phytase is a polypeptide having phytase activity, i.e. an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (http://www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, three different types of phytases are known: A so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 16 to 22 of SEQ ID NOs:2, 3, 4, 6 and amino acids 38-44 of SEQ ID NO: 9). In a preferred embodiment, the conserved active site motif is R-H-G-V-R-A-P, i.e. amino acids 16-22 (by reference to SEQ ID NO: 2) are RHGVRAP.

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate $(C_6H_6O_{24}P_6Na_{12})$ in a concentration of 0.0050 mol/l. Suitable phytase assays are the FYT and FTU assays described in Example 1 of WO 00/20569. FTU is for determining phytase activity in feed and premix. Phytase activity may also be determined using the assays of Example 1 ("Determination of phosphatase activity" or "Determination of phytase activity").

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence") and the amino acid sequence referred to in the claims (SEQ ID NO: 2) is calculated as the number of exact matches in an alignment of the two sequences, divided by the length of the "invention sequence," or the length of the SEQ ID NO: 2, whichever is the shortest. The result is expressed in percent identity.

An exact match occurs when the "invention sequence" and SEQ ID NO: 2 have identical amino acid residues in the same positions of the overlap (in the alignment example below this is represented by "|"). The length of a sequence is the number of amino acid residues in the sequence (e.g. the length of amino acids 1-411 of SEQ ID NO: 2 is 411).

Example 13 is an example of an alignment of the phytase of SEQ ID NO: 2 and the phytase of SEQ ID NO: 9, and the example illustrates how to calculate the percentage of identity between these two backbones.

In another, purely hypothetical, alignment example below, the overlap is the amino acid sequence "HTWGER-NL" of Sequence 1; or the amino acid sequence "HGWGEDANL" of Sequence 2. In the example a gap is indicated by a "-".

Hypothetical alignment example:

```
Sequence 1:    ACMSHTWGER-NL
                   | ||| ||
Sequence 2:       HGWGEDANLAMNPS
```

In a particular embodiment, the percentage of identity of an amino acid sequence of a polypeptide with, or to, SEQ ID NO: 2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In the above hypothetical example, the number of exact matches is 6, the length of the shortest one of the two amino acid sequences is 12; accordingly the percentage of identity is 50%.

In particular embodiments of the phytase of the invention, the degree of identity to SEQ ID NO: 2 is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 98.0%, 98.2%, 98.4%, 98.6%, 98.8%, 99.0%, 99.1%, 99.2%, 99.3%, 99.4%, 99.5%, 99.6%, 99.7%, 99.8%, or at least 99.9%. In alternative embodiments, the degree of identity is at least 70%, 71%, 72%, or at least 73%.

In still further particular embodiments, the phytase of the invention has no more than 1, 2, 3, 4, 5, 6, 7, 8, 9, or no more than 10 alterations as compared to SEQ ID NO: 2; no more than 11, 12, 13, 14, 15, 16, 17, 18, 19, or no more than 20 alterations as compared to SEQ ID NO: 2; no more than 21, 22, 23, 24, 25, 26, 27, 28, 29, or no more than 30 alterations as compared to SEQ ID NO: 2; no more than 31, 32, 33, 34, 35, 36, 37, 38, 39, or not more than 40 alterations as compared to SEQ ID NO: 2; no more than 41, 42, 43, 44, 45, 46, 47, 48, 49, or no more than 50 alterations as compared to SEQ ID NO: 2; no more than 51, 52, 53, 54, 55, 56, 57, 58, 59, or no more than 60 alterations as compared to SEQ ID NO: 2; no more than 61, 62, 63, 64, 65, 66, 67, 68, 69, or no more than 70 alterations as compared to SEQ ID NO: 2; no more than 71, 72, 73, 74, 75, 76, 77, 78, 79, or no more than 80 alterations as compared to SEQ ID NO: 2; no more than 81, 82, 83, 84, 85, 86, 87, 88, 89, or no more than 90 alterations as compared to SEQ ID NO: 2; no more than 91, 92, 93, 94, 95, 96, 97, 98, 99, or no more than 100 alterations as compared to SEQ ID NO: 2; no more than 101, 102, 103, 104, 105, 106, 107, 108, 109, or no more than 110 alterations as compared to SEQ ID NO: 2; no more than 111, 112, 113, 114, 115, 116, 117, 118, 119, or no more than 120 alterations as compared to SEQ ID NO: 2; or no more than 121, 122, 123, or 124 alterations as compared to SEQ ID NO: 2.

Position Numbering

The nomenclature used herein for defining amino acid positions is based on the amino acid sequence of the phytase derived from *Citrobacter braakii* ATCC 51113, the mature sequence of which is given in the sequence listing as SEQ ID NO: 2 (amino acids 1-411 of SEQ ID NO: 2). Accordingly, in the present context, the basis for numbering positions is SEQ ID NO: 2 starting with E1 and ending with E411.

When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g. SignalP). The expected signal peptide part of SEQ ID NO: 2 is included in the present sequence listing as SEQ ID NO: 8, which is encoded by SEQ ID NO: 7. SEQ ID NO: 2 is the expected mature part. Generally, the first amino acid of the mature part of an enzyme can be determined by N-terminal sequencing of the purified enzyme. Any difference between the signal peptide part and the mature part must then be due to to the presence of a propeptide.

Alterations, Such as Substitutions, Deletions, Insertions

A phytase variant can comprise various types of alterations relative to a template (i.e. a reference or comparative amino acid sequence such as SEQ ID NO: 2): An amino acid can be substituted with another amino acid; an amino acid can be deleted; an amino acid can be inserted; as well as any combination of any number of such alterations. In the present context the term "insertion" is intended to cover also N— and/or C-terminal extensions.

The general nomenclature used herein for a single alteration is the following: XDcY, where "X" and "Y" independently designate a one-letter amino acid code, or a "*" (deletion of an amino acid), "D" designates a number, and "c" designates an alphabetical counter (a, b, c, and so forth), which is only present in insertions. Reference is made to Table 1 below which describes purely hypothetical examples of applying this nomenclature to various types of alterations.

TABLE 1

| Type | Description | Example |
|---|---|---|
| Sub-<br>stitution | X = Amino acid in template<br>D = Position in template<br>c empty<br>Y = Amino acid in variant | G80A<br>　　　　80<br>AALNNSIGVLGVAPSAELYAVKVLGASGSG<br>‖‖‖‖‖‖‖:‖‖‖‖‖‖‖‖‖‖‖‖‖‖‖‖‖‖‖‖‖<br>AALNNSIAVLGVAPSAELYAVKVLGASGSG<br>(SEQ ID NOS: 25 and 26) |
| Insertion | X = "*"<br>D = Position in template<br>before the insertion<br>c = "a" for first insertion at<br>this position, "b" for next,<br>etc | *80aT *80bY *85aS<br>　　　　80　　　　85<br>AALNNSIG..VLGVA.PSAELYAVKVLGASG<br>‖‖‖‖‖‖‖‖　‖‖‖‖‖ ‖‖‖‖‖‖‖‖‖‖‖‖‖‖‖<br>AALNNSIGTYVLGVASPSAELYAVKVLGASG<br>(SEQ ID NOS: 27 and 28) |
| Deletion | X = Amino acid in template<br>D = Position in template<br>c empty<br>Y = "*" | V81*<br>　　　　80<br>AALNNSIGVLGVAPSAELYAVKVLGASGSG<br>‖‖‖‖‖‖‖‖ ‖‖‖‖‖‖‖‖‖‖‖‖‖‖‖‖‖‖‖‖‖<br>AALNNSIG.LGVAPSAELYAVKVLGASGSG<br>(SEQ ID NOS: 29 and 30) |
| N-terminal<br>extension | Insertions at position "0". | *0aA *0bT *0cG<br>　　　1<br>...AQSVPWGISRVQ<br>　　‖‖‖‖‖‖‖‖‖‖‖<br>ATGAQSVPWGISRVQ<br>(SEQ ID NOS: 31 and 32) |

TABLE 1-continued

| Type | Description | Example |
|---|---|---|
| C-terminal extension | Insertions after the N-terminal amino acid. | *275aS *275bT<br><br>                      270   275<br>ATSLGSTNLYGSGLVNAEAATR..<br>\|\|\|\|\|\|\|\|\|\|\|\|\|\|\|\|\|\|\|\|\|\|\|\|\|\|\|\|\|\|\|<br>ATSLGSTNLYGSGLVNAEAATRST<br>(SEQ ID NOS: 33 and 34) |

As explained above, the position number ("D") is counted from the first amino acid residue of SEQ ID NO: 2.

Several alterations in the same sequence are separated by "/" (slash), e.g. the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative alterations are separated by "," (comma), e.g., the designation "119R,K" means that the amino acid in position 119 is substituted with R or K.

The commas used herein in various other enumerations of possibilities mean what they usually do grammatically, viz. often and/or. E.g., the first comma in the listing "53V,Q, 121D, and/or 167Q" denotes an alternative (V or Q), whereas the two next commas should be interpreted as and/or options: 53 V or Q, and/or 121D, and/or 167Q.

In the present context, "at least one" (e.g. alteration) means one or more, e.g. 1, 2, 3, 4, 5, 6, 7, 8, 9, or 10 alterations; or 12, 14, 15, 16, 18, 20, 22, 24, 25, 28, or 30 alterations; and so on, up to a maximum number of alterations of 125, 130, 140, 150, 160, 170, 180, 190, or of 200. The phytase variants of the invention, however, still have to be at least 74% identical to SEQ ID NO: 2, this percentage being determined as described above.

A substitution or extension without any indication of what to substitute or extend with refers to the insertion of any natural, or non-natural, amino acid, except the one that occupies this position in the template.

Example 13 provides further illustration of how to apply this nomenclature.

Identifying Corresponding Position Numbers

As explained above, the mature phytase of *Citrobacter braakii* ATCC 51113 (SEQ ID NO: 2) is used as the standard for position numbering and, thereby, also for the nomenclature.

For another phytase, in particular a phytase variant of the invention, the position corresponding to position D in SEQ ID NO: 2 is found by aligning the two sequences as specified above in the section entitled "Phytase polypeptides, percentage of identity". From the alignment, the position in the sequence of the invention corresponding to position D of SEQ ID NO: 2 can be clearly and unambiguously identified (the two positions on top of each other in the alignment).

Example 13 is an example of an alignment of the phytase of SEQ ID NO: 2 and the phytase of SEQ ID NO: 9, and the example illustrates how corresponding positions in these two backbones are identified.

Below some additional, purely hypothetical, examples are included which are derived from Table 1 above which in the third column includes a number of alignments of two sequences:

Consider the third cell in the first row of Table 1: The upper sequence is the template, the lower the variant. Position number 80 refers to amino acid residue G in the template. Amino acid A occupies the corresponding position in the variant. Accordingly, this substitution is designated G80A.

Consider now the third cell in the second row of Table 1: The upper sequence is again the template and the lower the variant. Position number 80 again refers to amino acid residue G in the template. The variant has two insertions, viz. TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of Table 1: Position number 275 refers to the last amino acid of the template. A C-terminal extension of ST are said to be in position number 275a and 275b, respectively, although, again, of course they have their own "real" position number in the variant amino acid sequence.

Amended Properties, Reference Phytase

In a particular embodiment, the phytase of the invention has amended, preferably improved, properties. The terms "amended" and "improved" imply a comparison with another phytase. Examples of such other, reference, or comparative, phytases are: SEQ ID NO: 3, and/or SEQ ID NO: 4. Still further examples of reference phytases may be SEQ ID NO: 2, and/or SEQ ID NO: 6. A still further example of a reference phytase may be SEQ ID NO: 9, and the variants thereof disclosed in FIG. 1.

Non-limiting examples of properties that are amended, preferably improved, are the following: Thermostability, pH profile, specific activity, performance in animal feed, protease-sensibility, and/or glycosylation pattern. The phytase of the invention may also have an amended, preferably improved, temperature profile, and/or it may incorporate a change of a potential protease cleavage site.

Thermostability

Thermostability, or temperature stability, may be determined as described in Example 1 under the heading of "Determination of temperature stability." Accordingly, in a preferred embodiment, a phytase of the invention has a residual activity which is higher than the residual activity of a reference phytase, wherein residual activity is determined as follows: A fermentation supernatant is divided in two parts, one part is incubated for 30 minutes at a desired elevated temperature, and the other part for 30 minutes at 5° C., following which the activity of both is determined on p-nitrophenyl phosphate at 37° C. and pH 5.5, and the activity of the sample having been incubated at an elevated temperature is divided by the activity of the same sample having been incubated at 5° C. Preferred elevated temperatures are 50° C., 55° C., 60° C., 65° C., 70° C., 75° C., 80° C., or 85° C. If desired, the enzyme-containing samples may be diluted in 0.1 M NaAc pH 5.5. The residual activity of a phytase of the invention is preferably at least 105%, or at least 110%, 120%, 130%, 140%, 150% of the residual activity of the reference phytase.

In still further embodiments, the residual activity of a phytase of the invention is at least 200%, or at least 250%, 300%, 400%, or at least 500% of the residual activity of the reference phytase. In still further embodiments, the residual activity of a phytase of the invention is at least 2×, 3×, 4×, 5×, 6×, 7×, 10×, 15×, 20×, or at least 25× the residual activity of the reference phytase.

Thermostability may also be determined as described in Example 5. Accordingly, in a preferred embodiment, a phytase of the invention has a residual activity which is higher than the residual activity of a reference phytase, wherein residual activity is determined as follows: A fermentation supernatant is divided in two parts, one part is incubated for 30 minutes at a 50° C., and the other part for 30 minutes at 5° C., following which the activity of both is determined on p-nitrophenyl phosphate at 37° C. and pH 5.5, and the activity of the sample having been incubated at an elevated temperature is divided by the activity of the same sample having been incubated at 5° C. If desired, the enzyme-containing samples may be diluted in 0.1M NaAc pH 5.5. The residual activity of a phytase of the invention is preferably at least 2×, 3×, 4×, 5×, 6×, 7×, 10×, 15×, 20×, or at least 25× the residual activity of the reference phytase of SEQ ID NO: 3. The residual activity of a phytase of the invention is preferably at least 105%, or at least 110%, 120%, 130%, 140%, 150%, 160%, 170%, 180%, 190%, or at least 200% of the residual activity of the reference phytase of SEQ ID NO: 2. The following substitutions are particularly preferred as they improve thermostability as compared to the phytase of SEQ ID NO: 3 as well as to the phytase of SEQ ID NO: 2 (see Table 3): 4P, 5P, 111P, 1*, 1*/2*, 1*/2*/3*, 273L, and/or 286Q.

Thermostability may also be determined as described in Example 8. Accordingly, in a preferred embodiment, a phytase of the invention has a residual activity which is higher than the residual activity of a reference phytase, wherein residual activity is determined as follows: A fermentation supernatant is divided in two parts, one part is incubated for 30 minutes at a 60° C., and the other part for 30 minutes at 5° C., following which the activity of both is determined on p-nitrophenyl phosphate at 37° C. and pH 5.5, and the activity of the sample having been incubated at an elevated temperature is divided by the activity of the same sample having been incubated at 5° C. If desired, the enzyme-containing samples may be diluted in 0.1M NaAc pH 5.5, optionally including 0.005% Tween-20. The phytase of the invention and the reference phytase may be expressed in a Bacillus subtilis host strain. The host strain may be grown in 100 ml PS1 medium (100 g/L sucrose, 40 g/L Soy flakes, 10 g/L $Na_2HPO_4.12H_2O$, 0.1 ml/L Dowfax 63N10 (Dow)) in 500 ml shake flasks for four days at 30° C. at 300 rpm. The residual activity of a phytase of the invention is preferably at least 32%, or at least 34%, 36%, 38%, or at least 40% of the residual activity of the reference phytase of SEQ ID NO: 2. More preferably, the residual activity of a phytase of the invention is at least 50%, or at least 60%, 70%, 80%, 90%, or at least 100% of the residual activity of the reference phytase of SEQ ID NO: 2. Even more preferably the residual activity of a phytase of the invention is at least 120%, 140%, 160%, 180%, or at least 200% of the residual activity of the reference phytase of SEQ ID NO: 2. Most preferably, the residual activity of a phytase of the invention is at least 2×, or at least 3×, 4×, or at least 5× the residual activity of the reference phytase of SEQ ID NO: 2. The following substitutions are particularly preferred (see Table 5):

(i) 409E, 136P;
(ii) 411K, 331K/55D, 167Q, 179K/180T/181D/182K/183L/184*/185*/186*, 107E;
(iii) 196Q, 276R, 285G, 299L, 200K;
(iv) 119R, 121D, 107D, 179K/180E/181K/182H/183Q/184*/185*/186*;
(v) 314N, 161P, 410D, 141C, 179K/180E/181K/182Q/183Q/184*/185*/186*, 285N;
(vi) 164E, 411R, 52C, 137P, 314G;
(vii) 1K, 1*/2*/3*, 121T, 406A, 82E, 109A;
(viii) 5P, 57Y, 379R, 1*/2*;
(ix) 410E, 1*, 119K, 52E;
(x) 4P, 362K, 202N, 276K, 385D;
(xi) 111P/241Q, 162C, 179K/180E/181K/182K/183V/184*/185*/186*, 241Q;
(xii) 223E, 286Q, 107G, 114T/115Q/116A/117D/118T/119S/120S/121P/122D/123P/124L, 379K, 273L;
(xiii) 31C, 53V, 59C/100C;
(xiv) 46E, 111P, 114T/115Q/116T/117D/118T/119S/120S/121P/122D/123P/124L, 76G, 362R;
(xv) 141C/199C, 52C/99C.

Thermostability may also be determined as described in Example 9, i.e. using DSC measurements to determine the denaturation temperature, Td, of the purified phytase protein. The Td is indicative of the thermostability of the protein: The higher the Td, the higher the thermostability. Accordingly, in a preferred embodiment, the phytase of the invention has a Td which is higher than the Td of a reference phytase, wherein Td is determined on purified phytase samples (preferably with a purity of at least 95%, determined by SDS-PAGE), after dialysis in 20 mM Na-acetate pH 4.0 (preferably in a 2-3 h step followed by an over night step), followed by 0.45 um filtration and dilution with dialysis buffer to a protein concentration corresponding to approximately 2 absorbancy units ($A_{280}$), using Differential Scanning calorimetry at a 90° C./h scan rate from 20-90° C. in 20 mM Na-acetate buffer, pH 4.0. In a preferred embodiment, the Td of the phytase of the invention is higher than the Td of the phytase of SEQ ID NO: 4, more preferably at least 101% thereof, or at least 102%, 103%, 104%, 105%, 106%, 107%, 108%, 109%, or at least 110% thereof. Even more preferably, the Td of the phytase of the invention is at least 120%, 130%, 140%, 150%, 160%, 170%, 180%, or at least 190% of the Td of the phytase of SEQ ID NO: 4. The following substitutions are particularly preferred (see Table 6): 362K, 362R, 111P, and/or 273L. In still further particular embodiments, the thermostable phytase of the invention has a melting temperature, Tm (or a denaturation temperature, Td), as determined using Differential Scanning calorimetry (DSC) as described in Example 2 (i.e. in 20 mM sodium acetate, pH 4.0), of at least 50° C. In still further particular embodiments, the Tm is at least 51, 52, 53, 54, 55, 56, 57, 58, 59, 60, 61, 62, 62.5, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C. DSC measurements may also be performed as described in Example 1 ("DSC measurements"), or Example 2 ("Thermostability by DSC").

Thermostability may also be determined as described in Example 12. Accordingly, in a preferred embodiment the phytase of the invention, after incubation for 60 minutes at 70° C. and pH 4.0, has an improved residual activity as compared to the residual activity of a reference phytase treated in the same way, the residual activity being calculated for each phytase relative to the activity found before the incubation (at 0 minutes). The residual activity is preferably measured on sodium phytate at pH 5.5 and 37° C. The incubation is preferably in 0.1 M sodium acetate, pH 4.0. The phytase is preferably purified, more preferably to a purity of at least 95%, determined by SDS-PAGE. A preferred phytase activity assay buffer is 0.25 M Na-acetate pH 5.5. Using this method, the residual activity of the phytase of the invention is preferably at least 105% of the residual activity of the reference phytase, more preferably at least 110%, 115%, 120%, 130%, 140%, 150%, 160%, 170%, 180%, 190%, or at least 200%. In the alternative, the residual activity relative to the activity at 0 minutes is preferably at least 31%, or at least 32%. The following substitutions providing improved thermostability stability are preferred (see Table 9): 273L, 46E, 362R, and/or 53V.

In a particular embodiment, the phytase variant of the invention is more thermostable than the reference phytase, wherein thermostability is determined using any of the above-mentioned four tests (based on Example 1, 5, 8, 9, or 12).

In particular embodiments, an improved thermostability is expected of the following variants of the phytase of SEQ ID NO: 2 (in order of preference, within each grouping):
(i) K141C/V199C, Q91C/W46C, G52C/A99C, N31C/E176C, N31C/T177C, G59C/F100C, S162C/S247C;
(ii) D41P, Q91P, N136P, T137P, L154P, S161P, T355P, Q111P, K240P, G282P, T283P, T284P, G289P, N4P, G5P;
(iii) G52E, V55I, E57Y, L104A/A105F, K107D,G, Q109A,G, T76G, A84Y, N121T, I362K, M273L,Q, E285G,R, N286Q, V294T, I299L, E331K/V55D, F351Y;
(iv) E1*, E1*/E2*, E1*/E2*/Q3*;
(v) replacing the loop comprised between C178 and C187 with shorter loops selected from, e.g., QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), KTDKL (SEQ ID NO: 24);
(vi) E119R,K, E411R,K;
(vii) K107E, R164E,D;
(iix) I362R,K, T276R,K, I379R,K, V409D,E, Q223E, N385D, W46D,E, T410D,E, Q82E.
(ix) replacing the loop between residues 114 and 124 (YQKDEEKNDPL) which faces the active site with a loop selected from, e.g., HQEKMGTMDPT (SEQ ID NO: 10), HQQDIKQVDSL (SEQ ID NO: 11), HQPEIGKMDPV (SEQ ID NO: 12), TQADTSSPDPL (SEQ ID NO: 13), HQQDIKQADPL (SEQ ID NO: 14), TQTDTSSPDPL (SEQ ID NO: 15), NQADLKKTDPL (SEQ ID NO: 16);
(x) R339D.

Temperature Profile

Whether or not a phytase of the invention has an amended temperature profile as compared to a reference phytase may be determined as described in Example 10. Accordingly, in a particular embodiment the phytase of the invention has an amended temperature profile as compared to a reference phytase, wherein the temperature profile is determined as phytase activity as a function of temperature on sodium phytate at pH 5.5 in the temperature range of 20-90° C. (in 10° C. steps). A preferred buffer is in 0.25 M Na-acetate buffer pH 5.5. The activity at each temperature is preferably indicated as relative activity (in %) normalized to the value at optimum temperature. The optimum temperature is that temperature within the tested temperatures (i.e. those with 10° C. jumps) where the activity is highest.

In a preferred embodiment, the phytase of the invention has a relative activity at 70° C. of at least 18%, or at least 19%, 20%, 21%, 22%, 23%, 24%, or at least 25%. As explained above, this is relative to the activity at the optimum temperature. More preferably, the phytase of the invention has a relative activity at 70° C. of at least 26%, 27%, 28%, 29%, 30%, 31%, or at least 32%. Preferred substitutions which provide an amended temperature profile (in the form of a higher relative activity at 70° C.) are (see Table 7): 57Y, 76G, 107G, 273L, 362K, 46E, 362R, 53V, and/or 241Q. Their relative activity at 70° C. is higher as compared to the reference phytase of SEQ ID NO: 3 and 4, and in some instances (57Y, 76G, 107G, 273L, 362K, 362R, and/or 53V) also as compared to the reference phytase of SEQ ID NO: 2.

pH Profile

Whether or not a phytase of the invention has an amended pH profile as compared to a reference phytase may be determined as described in Example 11. Accordingly, in a particular embodiment the phytase of the invention has an amended pH profile as compared to a reference phytase, wherein the pH profile is determined as phytase activity as a function of pH on sodium phytate at 37° C. in the pH range of 2.0 to 7.5 (in 0.5 pH-unit steps). A preferred buffer is a cocktail of 50 mM glycine, 50 mM acetic acid and 50 mM Bis-Tris. Another preferred buffer is 0.25 M sodium acetate. The activity at each pH is preferably indicated as relative activity (in %) normalized to the value at optimum pH.

An example of an amended pH profile is where the pH curve (relative activity as a function of pH) is shifted towards higher, or lower, pH. Preferred substitutions which provide a shift of 0.5 pH units towards a higher pH as compared to the reference phytase of SEQ ID NO: 2, 3 or 4 are (see Table 8): 46E, and/or 218Q.

Another example of an amended pH profile is where the optimum pH is changed, in the upward or the downward direction. Preferred substitutions which provide a lower optimum pH as compared to SEQ ID NO: 2, 3, and 4 are (see Table 8): 46E, 121D, and/or 200K. Preferred substitutions which provide a higher optimum pH as compared to SEQ ID NO: 2, 3, and 4 are (see Table 8): 218Q, and/or 241Q.

An amended pH profile may also be determined as described in Example 1 ("Amended pH profile: Determination of pH 3.5/5.5 activity ratio"), viz. by comparing phosphatase activity at pH 3.5 and 5.5. Alternatively, the activity at pH 3.5 may be compared with the activity at pH 4.0, 4.5, or 5.0. In a still further alternative embodiment, phytase activities are compared instead of phosphatase activities.

In a particular embodiment, the phytase of the invention has an amended pH profile as compared to a reference phytase. More in particular, the pH profile is amended in the pH-range of 3.5-5.5. Still more in particular, the activity at pH 4.0, 4.5, 5.0, and/or 5.5 is at a level of at least 50%, 55%, 60%, 65%, 70%, 75%, 80%, 85%, 90%, or at least 95% of the activity at the pH-optimum (pH 3.5).

The pH profile, as well as the pH-optimum, of a polypeptide may be determined by incubating it at various pH-values, using a substrate in a pre-determined concentration and a fixed incubation temperature. The pH profile is a graphical representation of phytase activity versus pH, the pH-optimum is determined from the pH profile. In a particular embodiment, the phosphatase or phytase assay of Example 1 is used, e.g. the substrate is 5 mM sodium phytate, the reaction temperature 37° C., and the activity is determined at various pH-values, for example pH 2-12, replacing the pH 5.5 acetate buffer with a suitable buffer. Examples of suitable buffers are: 0.1 M glycine/HCl (pH 2.0-3.5), 0.1 M NaAc/Ac (pH 4.0-5.0), 0.1 M Bis-Tris/HCl (pH 5.5-6.5), 0.1 M Tris/HCl (pH 7.0). Other examples of buffers are: 100 mM succinic acid, 100 mM HEPES, 100 mM CHES, 100 mM CABS adjusted to pH-values 2.0, 2.5, 3.0, 3.5, 4.0, 5.0, 6.0, 7.0, 8.0, 9.0, 10.0, 11.0, and 12.0 with HCl or NaOH.

In particular embodiments, an amended pH profile is expected of the following variants of the phytase of SEQ ID NO: 2 (in order of preference, within each grouping):
(i) E218Q, D324N, T200R,K, N121D, E196Q, D202N, E406A, E167Q, E53V,Q, E241Q, D314N,G, E239Q, E285N;

(ii) replacing the loop between residues 114 and 124 (YQKDEEKNDPL) which faces the active site with a loop selected from, e.g., HQEKMGTMDPT (SEQ ID NO: 10), HQQDIKQVDSL (SEQ ID NO: 11), HQPEIGKMDPV (SEQ ID NO: 12), TQADTSSPDPL (SEQ ID NO: 13), HQQDIKQADPL (SEQ ID NO: 14), TQTDTSSPDPL (SEQ ID NO: 15), NQADLKKTDPL (SEQ ID NO: 16).

Specific Activity

In a particular embodiment, the phytase of the invention has an improved specific activity relative to a reference phytase. More in particular, the specific activity of a phytase of the invention is at least 105%, relative to the specific activity of a reference phytase determined by the same procedure. In still further particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the reference phytase as determined by the same procedure.

In the alternative, the term high specific activity refers to a specific activity of at least 200 FYT/mg Enzyme Protein (EP). In particular embodiments, the specific activity is at least 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 FYT/mg EP.

Specific activity is measured on highly purified samples (an SDS poly acryl amide gel should show the presence of only one component). The enzyme protein concentration may be determined by amino acid analysis, and the phytase activity in the units of FYT, determined as described in Example 1. Specific activity is a characteristic of the specific phytase variant in question, and it is calculated as the phytase activity measured in FYT units per mg phytase variant enzyme protein. See Example 7 for further details.

In particular embodiments, an amended specific activity is expected of the following variants of the phytase of SEQ ID NO: 2, in which, in order of preference, the loop between residues 114 and 124 (YQKDEEKNDPL) which faces the active site is replaced with a loop selected from, e.g., HQEKMGTMDPT (SEQ ID NO: 10), HQQDIKQVDSL (SEQ ID NO: 11), HQPEIGKMDPV (SEQ ID NO: 12), TQADTSSPDPL (SEQ ID NO: 13), HQQDIKQADPL (SEQ ID NO: 14), TQTDTSSPDPL (SEQ ID NO: 15), NQADLKKTDPL (SEQ ID NO: 16).

Performance in Animal Feed

In a particular embodiment the phytase of the invention has an improved performance in animal feed as compared to a reference phytase. The performance in animal feed may be determined by the in vitro model of Example 6. Accordingly, in a preferred embodiment the phytase of the invention has an improved performance in animal feed, wherein the performance is determined in an in vitro model, by preparing feed samples composed of 30% soybean meal and 70% maize meal with added $CaCl_2$ to a concentration of 5 g calcium per kg feed; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase (e.g. the phytases having SEQ ID NO: 3 and 4).

The phytase of the invention and the reference phytase are of course dosed in the same amount, preferably based on phytase activity units (FYT). A preferred dosage is 125 FYT/kg feed. Another preferred dosage is 250 FYT/kg feed. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified phytase of the invention, relative to the degraded IP6-P value of the reference phytase, is at least 101%, or at least 102%, 103%, 104%, 105%, 110%, 115%, or at least 120%. In still further preferred embodiments, the degraded IP6-P value of the purified phytase of the invention, relative to the degraded IP6-P value of the reference phytase, is at least 125%, 130%, 140%, 150%, 160%, 170%, 180%, 190%, or at least 200%. Preferably, the degraded IP6-P value of the phytase of the invention, relative to the degraded IP6-P value of the SEQ ID NO: 2 phytase, is at least 105%, 110%, 113%, 115%, 120%, 125%, or at least 130%.

The following substitutions provide an improved or at least as good performance in animal feed in vitro (see Table 4A) as compared to the phytase of SEQ ID NO: 3: 4P, 5P, 111P, 1*, 1*/2*, 1*/2*/3*, 273L, 286Q.

The following substitutions also provide an improved or at least as good performance in animal feed in vitro (see Table 4B) as compared to the phytase of SEQ ID NO: 3: 57Y, 76G, 107G, 362K, 362R, 121D, 196Q, 200K, 202N, 314N, 406A, and 114T/115Q/116N117D/118T/119S/120S/121P/122D/123P/124L.

Even more preferred substitutions when it comes to animal feed performance are: 57Y, 76G, 362K, 362R, 121D, 196Q, 200K, 202N, and 406A.

The relative performance of a phytase of the invention may also be calculated as the percentage of the phosphorous released by the reference phytase.

In a still further particular embodiment, the relative performance of the phytase of the invention may be calculated as the percentage of the phosphorous released by the phytase of the invention, relative to the amount of phosphorous released by the reference phytase.

In still further particular embodiments, the relative performance of the phytase of the invention is at least 105%, preferably at least 110, 120, 130, 140, 150, 160, 170, 180, 190, or at least 200%.

Reduced Protease-sensibility

In a particular embodiment, the phytase of the invention has a reduced protease-sensibility. More in particular, it has a reduced sensibility towards the Kex2 protease, meaning a reduced tendency to become cleaved by this protease.

Variant 339D, preferably R339D, is an example of a phytase of the invention with a reduced protase-sensibility.

Glycosylation Pattern

Glycosylation is a phenomenon which is only observed when expressing proteins in eukaryotes such as fungi and transgenic plants, but not in prokaryotes such as bacteria. There are various types of glycosylation, but in the present context the most relevant is the N-glycosylation, i.e. the asparagine-linked glycosylation where sugars are attached to a protein, starting from an N-acetyglucosamine molecule attached to asparagines. N-glycosylation has been found to occur only to asparagines that in the sequence are part of the following tripeptides: N-X-T or N-X-S, where X designates any amino acid.

Surprisingly, a lower thermostability was observed when the phytase of SEQ ID NO: 2 was expressed in the fungus (yeast) *Pichia pastoris*, as compared to when it was expressed in *Bacillus subtilis*, see Example 2.

This observation has led to the proposal of the present invention that thermostability may be improved for phytases expressed in fungi by altering potential glycosylation sites.

The present invention accordingly also relates to phytase variants having an amended glycosylation pattern, preferably amended N-glycosylation sites. The amended glycosylation is expected to confer an improved thermostability upon the phytase variant, when expressed in a fungus.

Examples of phytases are bacterial phytases, e.g. Gram-negative phytases, such as *E. coli* and *Citrobacter* phytases and variants thereof, including the phytases of the present invention as well as the phytases of SEQ ID NO: 2, SEQ ID NO: 3, SEQ ID NO: 4, SEQ ID NO: 6, and SEQ ID NO: 9 herein. Examples of fungal expression hosts are *Pichia*, *Saccharomyces*, and *Aspergillus* species.

In particular embodiments, an amended glycosylation pattern is expected of the following phytases of the invention (e.g. variants of SEQ ID NO: 2), in order of preference: N31T, N74A, N171T, N203T, N281H, N316D, N308A. The following are replacing an N-X-T type pattern: N31T, N74A, N281H. The following are replacing an N-X-S type pattern: N171T, N203T, N308A, N316D.

Low-allergenic Variants

In a specific embodiment, the phytases of the present invention are (also) low-allergenic variants, designed to invoke a reduced immunological response when exposed to animals, including man. The term immunological response is to be understood as any reaction by the immune system of an animal exposed to the phytase variant. One type of immunological response is an allergic response leading to increased levels of IgE in the exposed animal. Low-allergenic variants may be prepared using techniques known in the art. For example the phytase variant may be conjugated with polymer moieties shielding portions or epitopes of the phytase variant involved in an immunological response. Conjugation with polymers may involve in vitro chemical coupling of polymer to the phytase variant, e.g. as described in WO 96/17929, WO 98/30682, WO 98/35026, and/or WO 99/00489. Conjugation may in addition or alternatively thereto involve in vivo coupling of polymers to the phytase variant. Such conjugation may be achieved by genetic engineering of the nucleotide sequence encoding the phytase variant, inserting consensus sequences encoding additional glycosylation sites in the phytase variant and expressing the phytase variant in a host capable of glycosylating the phytase variant, see e.g. WO 00/26354. Another way of providing low-allergenic variants is genetic engineering of the nucleotide sequence encoding the phytase variant so as to cause the phytase variants to self-oligomerize, effecting that phytase variant monomers may shield the epitopes of other phytase variant monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the phytase variant by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a phytase variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template phytase coding sequence or a subsequence thereof, wherein the mutant nucleic acid sequence encodes a variant phytase. The introduction of a mutation into the nucleic acid sequence to exchange one nucleotide for another nucleotide may be accomplished by any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence Expression Vector The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a phytase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a phytase, phosphatase, xylanase, galactanase, alpha-galactosidase, protease, phospholipase, amylase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The phytase variant may also be expressed as a fusion protein, i.e. that the gene encoding the phytase variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma har-* *zianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a phytase of the present invention comprising (a) cultivating a host cell under conditions conducive for production of the phytase; and (b) recovering the phytase.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. Nos. 5,689,054 and 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the *chlorella* virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g. from the milk of female animals, or the polypeptide may be expressed to the benefit of the animal itself, e.g. to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g. by use of a transgene expression vector which comprises a suitable milk protein promoter, and the gene encoding the polypeptide. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e. the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may e.g. include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

The phytase of the invention may also be combined with other phytases, for example ascomycete phytases such as *Aspergillus* phytases, for example derived from *Aspergillus ficuum*, *Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a synthethase.

Usally fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30

MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e. in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Particular Embodiments

The invention also relates to the following particular embodiments:

I. A phytase which has at least 74% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411;

preferably in at least one position selected from the following: 1, 2, 3, 4, 5, 31, 46, 52, 53, 55, 57, 59, 76, 82, 99, 100, 107, 109, 111, 114, 115, 116, 117, 118, 119, 120, 121, 122, 123, 124, 137, 141, 161, 162, 164, 167, 179, 180, 181, 182, 183, 184, 185, 186, 196, 199, 200, 202, 218, 223, 241, 273, 276, 285, 286, 299, 314, 331, 339, 362, 379, 385, 406, 410, and 411;

with the proviso that the phytase is not SEQ ID NO: 3, not SEQ ID NO: 4, and not SEQ ID NO: 6.

II. A phytase which has at least 74% identity to SEQ ID NO: 2 and which comprises at least one alteration as compared to SEQ ID NO: 2 in at least one position selected from the following: 1, 2, 3, 4, 5, 41, 46, 52, 53, 55, 57, 59, 74, 76, 82, 84, 91, 99, 100, 104, 105, 107, 109, 111, 114, 115, 116, 117, 118, 119, 120, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 324, 339, 351, 355, 362, 379, 385, 406, 409, 410, and 411;

preferably in at least one position selected from the following: 1, 2, 3, 4, 5, 46, 52, 53, 55, 57, 59, 76, 82, 99, 100, 107, 109, 111, 114, 115, 116, 117, 118, 119, 120, 122, 123, 124, 137, 141, 161, 162, 164, 167, 179, 180, 181, 182, 183, 184, 185, 186, 196, 199, 200, 202, 218, 223, 241, 273, 276, 285, 286, 299, 314, 339, 362, 379, 385, 406, 410, and 411.

III. A phytase which has at least 74% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411;

preferably in at least one position selected from the following preferably in at least one position selected from the following: 1, 2, 3, 4, 5, 31, 46, 52, 53, 55, 57, 59, 76, 82, 99, 100, 107, 109, 111, 114, 115, 116, 117, 118, 119, 120, 121, 122, 123, 124, 137, 141, 161, 162, 164, 167, 179, 180, 181, 182, 183, 184, 185, 186, 196, 199, 200, 202, 218, 223, 241, 273, 276, 285, 286, 299, 314, 331, 339, 362, 379, 385, 406, 410, and 411;

with the proviso that the phytase is not SEQ ID NO: 3, not SEQ ID NO: 4, not SEQ ID NO: 6, and not SEQ ID NO: 9 and the variants thereof listed in FIG. 1.

IV. A phytase which has at least 74% identity to SEQ ID NO: 2 and which comprises at least one alteration as compared to SEQ ID NO: 2 in at least one position selected from the following: 1, 2, 3, 4, 5, 41, 46, 52, 53, 55, 57, 59, 74, 76, 82, 84, 91, 99, 100, 104, 105, 107, 109, 111, 114, 115, 116, 117, 118, 119, 120, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 324, 339, 351, 355, 362, 379, 385, 406, 409, 410, and 411 preferably in at least one position selected from the following: 1, 2, 3, 4, 5, 46, 52, 53, 55, 57, 59, 76, 82, 99, 100, 107, 109, 111, 114, 115, 116, 117, 118, 119, 120, 122, 123, 124, 137, 141, 161, 162, 164, 167, 179, 180, 181, 182, 183, 184, 185, 186, 196, 199, 200, 202, 218, 223, 241, 273, 276, 285, 286, 299, 314, 339, 362, 379, 385, 406, 410, and 411;

with the proviso that the phytase is not SEQ ID NO: 9 and the variants thereof listed in FIG. 1.

V. A phytase which has at least 74% identity to SEQ ID NO: 2 and which comprises at least one alteration as compared to SEQ ID NO: 2 in at least one position selected from the following: 4, 5, 41, 46, 59, 82, 84, 91, 99, 105, 107, 109, 111, 115, 116, 117, 119, 122, 123, 124, 136, 137, 141, 161, 162, 164, 167, 171, 176, 179, 180, 186, 196, 199, 200, 218, 223, 239, 240, 241, 247, 273, 276, 281, 282, 283, 284, 289, 294, 299, 308, 314, 324, 339, 351, 355, 379, 385, 406, 409, 410, and 411;

preferably in at least one position selected from the following: 4, 5, 46, 59, 82, 99, 107, 109, 111, 115, 116, 117, 119, 122, 123, 124, 137, 141, 161, 162, 164, 167, 179, 180, 186, 196, 199, 200, 218, 223, 241, 273, 276, 299, 314, 339, 379, 385, 406, 410, and 411.

VI. A phytase which has at least 74% identity to SEQ ID NO: 2 and which comprises at least one of the following alterations: 1*, 2*, 3*, 4P, 5P, 31C,T, 41P, 46C,D,E, 52C,E, 53V,Q, 55I,D, 57Y, 59C, 74A, 76G, 82E, 84Y, 91C,P, 99C, 100C, 104A, 105F, 107D,E,G, 109A,G, 111P, 114H,N,T, 115Q, 116A,E,P,T,Q 117D,E,K 118I,L,M,T, 119G,K,R,S, 120K,S,T,Q, 121A,D,M,P,T,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 331K, 339D, 351Y, 355P, 362K,R, 379K,R, 385D, 406A, 409D,E, 410D,E, and/or 411R,K; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);

preferably at least one of the following alterations: 1*, 2*, 3*, 4P, 5P, 31C, 46E, 52C,E, 53V, 55D, 57Y, 59C, 76G, 82E, 99C, 100C, 107D,E,G, 109A, 111P, 114T, 115Q, 116AT, 117D, 118T, 119K,R,S, 120S, 121D,P,T,122D, 123P, 124L, 137P, 141C, 161P, 162C, 164E, 167Q, 179K, 180E,T, 181D,K, 182H,K,Q, 183L,V,Q, 184*, 185*, 186*, 196Q, 199C, 200K, 202N, 218Q, 223E, 241Q, 273L, 276K,R, 285G,R, 286Q, 299L, 314G,N, 331K, 339D, 362K,R, 379K,R, 385D, 406A, 410D,E, and/or 411R,K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24);

with the proviso that the phytase is not SEQ ID NO: 3, not SEQ ID NO: 4, and not SEQ ID NO: 6.

VII. A phytase which has at least 74% identity to SEQ ID NO: 2 and which comprises at least one of the following alterations: 1*, 2*, 3*, 4P, 5P, 31C,T, 41P, 46C,D,E, 52C,E, 53V,Q, 55I,D, 57Y, 59C, 74A, 76G, 82E, 84Y, 91C,P, 99C, 100C, 104A, 105F, 107D,E,G, 109A,G, 111P, 114H,N,T, 115Q, 116A,E,P,T,Q 117D,E,K, 118I,M,L,T, 119G,K,R,S, 120K,S,T,Q, 121A,D,M,P,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 339D, 351Y, 355P, 362K,R, 379K,R, 385D, 406A, 409D,E, 410D,E, and/or 411K,R; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);

preferably at least one of the following alterations: 1*, 2*, 3*, 4P, 5P, 31C, 46E, 52C,E, 53V, 55D, 57Y, 59C, 76G, 82E, 99C, 100C, 107D,E,G, 109A, 111P, 114T, 115Q, 116AT, 117D, 118T, 119K,R,S, 120S, 121D,P, 122D, 123P, 124L, 137P, 141C, 161P, 162C, 164E, 167Q, 179K, 180E,T, 181D,K, 182H,K,Q, 183L,V,Q, 184*, 185*, 186*, 196Q, 199C, 200K 202N, 218Q, 223E, 241Q, 273L, 276K,R, 285G,R, 286Q, 299L, 314G,N, 339D, 362K,R, 379K,R, 385D, 406A, 410D,E, and/or 411R,K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24).

IIX. A phytase which has at least 74% identity to SEQ ID NO: 2 and which comprises at least one of the following alterations: 1*, 2*, 3*, 4P, 5P, 31C,T, 41P, 46C,D,E, 52C,E, 53V,Q, 55D,I, 57Y, 59C, 74A, 76G, 82E, 84Y, 91C,P, 99C, 100C, 104A, 105F, 107D,E,G, 109A,G, 111P, 114H,N,T, 115Q, 116A,E,P,T,Q, 117D,E,K, 118I,L,M,T, 119G,K,R,S, 120K,S,T,Q, 121A,D,M,P,T,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 331K, 339D, 351Y, 355P, 362K,R, 379K,R, 385D, 406A, 409D,E, 410D,E, and/or 411R,K; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);

preferably at least one of the following alterations: 1*, 2*, 3*, 4P, 5P, 31C, 46E, 52C,E, 53V, 55D, 57Y, 59C, 76G, 82E, 99C, 100C, 107D,E,G, 109A, 111P, 114T, 115Q, 116AT, 117D, 118T, 119K,R,S, 120S, 121D,P, 122D, 123P, 124L, 137P, 141C, 161P, 162C, 164E, 167Q, 179K, 180E,T, 181D,K, 182H,K,Q, 183L,V,Q, 184*, 185*, 186*, 196Q, 199C, 200K 202N, 218Q, 223E, 241Q, 273L, 276K,R, 285G,R, 286Q, 299L, 314G,N, 339D, 362K,R, 379K,R, 385D, 406A, 410D,E, and/or 411R,K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24).

with the proviso that the phytase is not SEQ ID NO: 3, not SEQ ID NO: 4, not SEQ ID NO: 6, and not SEQ ID NO: 9 and the variants thereof listed in FIG. 1.

IX. A phytase which has at least 74% identity to SEQ ID NO: 2 and which comprises at least one of the following alterations: 1*, 2*, 3*, 4P, 5P, 31C,T, 41P, 46C,D,E, 52C,E, 53V,Q, 55I,D, 57Y, 59C, 74A, 76G, 82E, 84Y, 91C,P, 99C, 100C, 104A, 105F, 107D,E,G, 109A,G, 111P, 114H,N,T, 115Q, 116A,E,P,T,Q 117D,E,K, 118 I,M,L,T, 119G,K,R,S, 120K,S,T,Q, 121A,D,M,P,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 339D, 351Y, 355P, 362K,R, 379K,R, 385D, 406A, 409D,E, 410D,E, and/or 411K,R; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);

preferably at least one of the following alterations: 1*, 2*, 3*, 4P, 5P, 31C, 46E, 52C,E, 53V, 55D, 57Y, 59C, 76G, 82E, 99C, 100C, 107D,E,G, 109A, 111P, 114T, 115Q, 116AT, 117D, 118T, 119K,R,S, 120S, 121D,P, 122D, 123P, 124L, 137P, 141C, 161P, 162C, 164E, 167Q, 179K, 180E,T, 181D,K, 182H,K,Q, 183L,V,Q, 184*, 185*, 186*, 196Q, 199C, 200K 202N, 218Q, 223E, 241Q, 273L, 276K,R, 285G,R, 286Q, 299L, 314G,N, 339D, 362K,R, 379K,R, 385D, 406A, 410D,E, and/or 411R,K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24).

with the proviso that the phytase is not SEQ ID NO: 9 and the variants thereof listed in FIG. 1.

X. A phytase which has at least 74% identity to SEQ ID NO: 2 and which comprises at least one of the following alterations: A phytase which has at least 74% identity to SEQ ID NO: 2 and which comprises at least one of the following alterations: 1*, 2*, 3*, 4P, 5P, 31C,T, 41P, 46C,D,E, 52C,E, 53Q, 55D, 57Y, 59C, 74A, 82E, 84Y, 91C,P, 99C, 100C, 104A, 105F, 107D,E,G, 109A,G, 111P, 114H,T, 115Q, 116A,E,P,T,Q 117D,E,K, 118 I,M,L,T, 119G,K,R,S, 120K,S,T,Q, 121A,D,M,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,K, 182K,S,Q, 183A,L,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N, R, 286K,Q, 289P, 294T, 299L, 308A, 314G,N, 316D, 324N, 339D, 351Y, 355P, 362K,R, 379K,R, 385D, 406A, 409D,E, 410D,E, and/or 411K,R; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);

preferably at least one of the following alterations: 1*, 2*, 3*, 4P, 5P, 31C, 46E, 52C,E, 55D, 57Y, 59C, 82E, 99C, 100C, 107D,E,G, 109A, 111P, 114T, 115Q, 116AT, 117D, 118T, 119K,R,S, 120S, 121D, 122D, 123P, 124L, 137P, 141C, 161P, 162C, 164E, 167Q, 179K, 180E,T, 181D,K, 182K,Q, 183L,V,Q, 184*, 185*, 186*, 196Q, 199C, 200K 202N, 218Q, 223E, 241Q, 273L, 276K,R, 285G,R, 286Q, 299L, 314G,N, 339D, 362K,R, 379K,R, 385D, 406A, 410D,E, and/or 411R,K; and/or wherein the amino acids in position 179, 180, 181, 182, 183, 184, 185, and 186 have been replaced by KEKHQ (SEQ ID NO: 21), KEKQQ (SEQ ID NO: 22), KEKKV (SEQ ID NO: 23), or KTDKL (SEQ ID NO: 24).

XI. A phytase which has at least 74% identity to SEQ ID NO: 2 and which comprises at least one of the following alterations: 1H,K,R, 60P, 105E, 106A,G, 155F, 157F, 173P, 175L, 188P, 205P, 215M, 231P, 254Y, 280P, 330D, and/or 371P;

preferably 1K;

with the proviso that the phytase is not SEQ ID NO: 3, not SEQ ID NO: 4, not SEQ ID NO: 6, and not SEQ ID NO: 9 and the variants thereof listed in FIG. 1.

XII. A phytase which has at least 74% identity to SEQ ID NO: 2 and which comprises at least one of the following alterations: 1H,R, 60P, 105E, 106A,G, 157F, 173P, 175L, 188P, 205P, 215M, 231P, 254Y, 280P.

XIII. A phytase which has at least 74% identity to SEQ ID NO: 2 and which comprises at least one of the following alterations: 52C, 141C, 162C, 31C, 52C, 99C, 59C, 100C, 141C/199C, 4P, 5P, 111P, 137P, 161P, 52E, 57Y, 76G, 107D, 107G, 109A, 1*, 1*/2*, 1*/2*/3*, 121T, 273L, 285G, 286Q, 299L, 362K, 331K/55D, 107E, 46E, 82E, 119R, 119K, 164E, 223E, 276R, 276K, 362R, 379R, 379K, 385D, 410D, 410E, 411R, 411K, 53V, 121D, 167Q, 196Q, 200K, 202N, 218Q, 241Q, 285N, 314N, 314G, 406A, 179K/180E/181K/182H/183Q/184*/185*/186*,
179K/180E/181K/182Q/183Q/184*/185*/186*,
179K/180E/181K/182K/183V/184*/185*/186*,
179K/180T/181D/182K/183L/184*/185*/186*, 111P/241Q, 1K,
114T/115Q/116A/117D/118T/119S/120S/121P/122D/123P/124L,
114T/115Q/116T/117D/118T/119S/120S/121P/122D/123P/124L.

XIV. The phytase of any one of embodiments 1-13 which is a variant of the phytase of SEQ ID NO: 2.

XV. The phytase of any one of embodiments 1-13 which is a variant of the phytase of SEQ ID NO: 3.

XVI. The phytase of any one of embodiments 1-13 which is a variant of the phytase of SEQ ID NO: 4.

XVII. The phytase of any one of embodiments 1-13 which is a variant of the phytase of SEQ ID NO: 6.

IIXX. The phytase of any one of embodiments 1-13 which is a variant of the phytase of SEQ ID NO: 9.

IXX. The phytase of any one of embodiments 1-13 which is a variant of any one of the phytase variants related to SEQ ID NO: 9 and listed in FIG. 1.

XX. The phytase of any one of embodiments 1-19 which furthermore comprises a substitution or a combination of substitutions selected from amongst the substitutions and combinations of substitutions listed in each row of FIG. 1.

XXI. The phytase of any one of embodiments 1-20, which has an improved thermostability, an improved pH profile, an improved specific activity, an amended glycosylation pattern, an improved temperature profile, an improved performance in animal feed, and/or which incorporates a change of a potential protease cleavage site.

XXII. An isolated nucleic acid sequence comprising a nucleic acid sequence which encodes the phytase of any of embodiments I-XXI.

XXIII. A nucleic acid construct comprising the nucleic acid sequence of embodiment XXII operably linked to one or more control sequences that direct the production of the phytase in a suitable expression host.

XXIV. A recombinant expression vector comprising the nucleic acid construct of embodiment XXIII.

XXV. A recombinant host cell comprising the nucleic acid construct of embodiment XXIII and/or the expression vector of embodiment XXIV.

XXVI. A method for producing the phytase of any one of embodiments I-XXI, comprising (a) cultivating the host cell of embodiment XXV to produce a supernatant comprising the phytase; and (b) recovering the phytase.

XXVII. A transgenic plant, or plant part, capable of expressing a phytase of any one of embodiments I-XXI.

IIXXX. A transgenic, non-human animal, or products, or elements thereof, being capable of expressing a phytase of any one of embodiments I-XXI.

IIXXX. A composition comprising at least one phytase of any one of embodiments I-XXI, and
(a) at least one fat soluble vitamin;
(b) at least one water soluble vitamin; and/or
(c) at least one trace mineral.

XXX. The composition of embodiment IXX further comprising at least one enzyme selected from the following group of enzymes: amylase, phytase, phosphatase, xylanase, galactanase, alpha-galactosidase, protease, phospholipase, and/or beta-glucanase.

XXXI. The composition of any one of embodiments IXX-XXX which is an animal feed additive.

XXXII. An animal feed composition having a crude protein content of 50 to 800 g/kg and comprising the phytase of any one of embodiments I-XXI or the composition of any one of embodiments IXXX-XXXI.

XXXIII. A method for improving the nutritional value of an animal feed, wherein the phytase of any one of embodiments I-XXI or the composition of any one of embodiments IXXX-XXXI is added to the feed.

XXXIV. A process for reducing phytate levels in animal manure comprising feeding an animal with an effective amount of the feed of embodiment XXXII.

XXXV. A method for the treatment of vegetable proteins, comprising the step of adding the phytase of any one of embodiments I-XXI or the composition of any one of embodiments IXXX-XXXI to at least one vegetable protein or protein source.

XXXVI. Use of the phytase of any one of embodiments I-XXI or the composition of any one of embodiments IXXX-XXXI in animal feed; in the preparation of animal feed; for improving the nutritional value of animal feed; for reducing phytate levels in animal manure; for the treatment of vegetable proteins; or for liberating phosphorous from a phytase substrate.

a). A phytase which has at least 70% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411; with the proviso that the phytase is not SEQ ID NO: 3, not SEQ ID NO: 4, and not SEQ ID NO: 6.

a1). A phytase which has at least 70% identity to SEQ ID NO: 2 and which comprises at least one alteration as compared to SEQ ID NO: 2 in at least one position selected from the following: 1, 2, 3, 4, 5, 31, 41, 46, 52, 53, 55, 57, 59, 74, 76, 82, 84, 91, 99, 100, 104, 105, 107, 109, 111, 114, 115, 116, 117, 118, 119, 120, 121, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 316, 324, 331, 339, 351, 355, 362, 379, 385, 406, 409, 410, and 411, with the proviso that the variant does not comprise (i) 31D/121T/316N/331E, and not (ii) 31D/121N/316K/331E, and not (iii) 31N/121N/316N/331K.

a2). A phytase which has at least 70% identity to SEQ ID NO: 2 and which comprises at least one alteration as compared to SEQ ID NO: 2 in at least one position selected from the following: 1, 2, 3, 4, 5, 41, 46, 52, 53, 55, 57, 59, 74, 76, 82, 84, 91, 99, 100, 104, 105, 107, 109, 111, 114, 115, 116, 117, 118, 119, 120, 122, 123, 124, 136, 137, 141, 154, 161, 162, 164, 167, 171, 176, 177, 179, 180, 181, 182, 183, 184, 185, 186, 196, 199, 200, 202, 203, 218, 223, 239, 240, 241, 247, 273, 276, 281, 282, 283, 284, 285, 286, 289, 294, 299, 308, 314, 324, 339, 351, 355, 362, 379, 385, 406, 409, 410, and 411.

a3). The phytase of embodiment a2), which comprises at least one of the following alterations: 1\*, 2\*, 3\*, 4P, 5P, 31C,T, 41P, 46C,D,E, 52C,E, 53V,Q, 55I,D, 57Y, 59C, 74A, 76G, 82E, 84Y, 91C,P, 99C, 100C, 104A, 105F, 107D,E,G, 109A,G, 111P, 114H,N,T, 115Q, 116A,E,P,T,Q 117D,E,K, 118 I,M,L,T, 119G,K,R,S, 120K,S,T,Q, 121A,D,M,P,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K,S,Q, 183A,L,P,S,V,Q, 184\*, 185\*, 186\*, 196Q, 199C, 200K,R, 202N, 203T, 218Q, 223E, 239Q, 240P, 241Q, 247C, 273L,Q, 276K,R, 281H, 282P, 283P, 284P, 285G,N,R, 286K,Q, 289P, 294T, 299L, 308A, 314G,N, 316D, 324N, 339D, 351Y, 355P, 362K,R, 379K,R, 385D, 406A, 409D,E, 410D,E, and/or 411K,R; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24).

a4). The phytase of any one of embodiments a2)-a3), which comprises at least one of the following alterations:
(i) 31C, 46C, 52C, 59C, 910, 99C, 100C, 141C, 162C, 176C, 177C, 199C, and/or 247C;
(ii) 4P, 5P, 41P, 91P, 111P, 136P, 137P, 154P, 161P, 240P, 282P, 283P, 284P, 289P, and/or 355P;
(iii) 52E, 55D,I, 57Y, 76G, 84Y, 104A, 105F, 107D,G, 109A, G, 273L,Q, 285G,R, 286Q, 294T, 299L, 351Y, and/or 362K;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) 119K,R, and/or 411K,R;
(vii) 107E, and/or 164D,E;
(viii) 46D,E, 82E, 223E, 276K,R, 362K,R, 379K,R, 385D, 409D,E, and/or 410D,E;
(ix) 53V,Q, 121D, 167Q, 196Q, 200K,R, 202N, 218Q, 239Q, 241Q, 285N, 314G,N, 324N, and/or 406A;
(x) 114H,N,T 115Q, 116A,E,P,T,Q, 117D,E,K, 118I,L,M,T 119G,K,S, 120K,S,T,Q, 121A,M,P,V, 122D, 123P,S, and/or 124L,T,V
(xi) 31T, 74A, 171T, 203T, 281H, 308A, and/or 316D; and/or
(xii) 339D.

a5). The phytase of any one of embodiments a2)-a4), which comprises at least one of the following alterations:
(i) 141C/199C, 91C/46C, 52C/99C, 31C/176C, 31C/177C, 59C/100C, and/or 162C/247C;
(ii) 41P, 91P, 136P, 137P, 154P, 161P, 355P, 111P, 240P, 282P, 283P, 284P, 289P, 4P, and/or 5P;
(iii) 52E, 55I, 57Y, 104A/105F, 107D,G, 109A,G, 76G, 84Y, 362K, 273L,Q, 285G,R, 286Q, 294T, 299L, 331K/55D, and/or 351Y;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) 119R,K, and/or 411R,K;
(vii) 107E, and/or 164E,D;
(viii) 362R,K, 276R,K, 379R,K, 409D,E, 223E, 385D, 46D, E, 410D,E, and/or 82E;
(ix) 218Q, 324N, 200R,K, 121D, 196Q, 202N, 406A, 167Q, 53V,Q, 241Q, 314N,G, 239Q, and/or 285N;
(x) 114H/115Q/116E/117K/118M/119G/120T/121M/122D/123P/124T, 114H/115Q/116Q/117D/118I/119K/120Q/121V/122D/123S/124L, 114H/115Q/116P/117E/118I/119G/120K/121M/122D/123P/124V, 114T/115Q/116A/117D/118T/119S/120S/121P/122D/123P/124L, 114H/115Q/116Q/117D/118I/119K/120Q/121A/122D/123P/124L, 114T/115Q/116T/117D/118T/119S/120S/121P/122D/123P/124L, or 114N/115Q/116N117D/118L/119K/120K/121T/122D/123P/124L;

(xi) 31T, 74A, 171T, 203T, 281H, 308A, and/or 316D; and/or
(xii) 339D.

b). The phytase of embodiment a) or a1), which comprises at least one of the following alterations: 1*, 2*, 3*, 4P, 5P, 31C,T, 41P, 46C,D,E, 52C,E, 53V,Q, 55D,I, 57Y, 59C, 74A, 76G, 82E, 84Y, 91C,P, 99C, 100C, 104A, 105F, 107D,E,G, 109A,G, 111P, 114H,N,T, 115Q, 116A,E,P,T, Q, 117D,E,K 118I,L,M,T 119G,K,R,S, 120K,S,T,Q, 121A,D,M,P,T,V, 122D, 123P,S, 124L,T,V, 136P, 137P, 141C, 154P, 161P, 162C, 164D,E, 167Q, 171T, 176C, 177C, 179G,I,K,N,Q, 180A,E,G,T, 181D,G,I,K, 182H,K, S,Q, 183A,L,P,S,V,Q, 184*, 185*, 186*, 196Q, 199C, 200K,R, 202N, 203T, 218Q, 223E, 239Q, 240P, 241Q, 247C, 273L,Q, 276K,R, 281H, 282P, 283P, 284P, 285G,N, R, 286K,Q, 289P, 294T, 299L, 308A, 314G,N, 316D, 324N, 331K, 339D, 351Y, 355P, 362K,R, 379K,R, 385D, 406A, 409D,E, 410D,E, and/or 411R,K; and/or wherein the amino acids in position 179, 180, 181, 182, 183, 184, 185, and 186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24).

c). The phytase of any one of the above embodiments, which comprises at least one of the following alterations:
(i) 31C, 46C, 52C, 59C, 91C, 99C, 100C, 141C, 162C, 176C, 177C, 199C, and/or 247C;
(ii) 4P, 5P, 41P, 91P, 111P, 136P, 137P, 154P, 161P, 240P, 282P, 283P, 284P, 289P, and/or 355P;
(iii) 52E, 55D,I, 57Y, 76G, 84Y, 104A, 105F, 107D,G, 109A, G, 121T, 273L,Q, 285G,R, 286Q, 294T, 299L, 331K, 351Y, and/or 362K;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) 119K,R, and/or 411K,R;
(vii) 107E, and/or 164D,E;
(viii) 46D,E, 82E, 223E, 276K,R, 362K,R, 379K,R, 385D, 409D,E, and/or 410D,E;
(ix) 53V,Q, 121D, 167Q, 196Q, 200K,R, 202N, 218Q, 239Q, 241Q, 285N, 314G,N, 324N, and/or 406A;
(x) 114H,N,T 115Q, 116A,E,P,T,Q, 117D,E,K, 118I,L,M,T 119G,K,S, 120K,S,T,Q, 121A,M,P,T,V, 122D, 123P,S, and/or 124L,T,V;
(xi) 31T, 74A, 171T, 203T, 281H, 308A, and/or 316D; and/or
(xii) 339D.

c1). The phytase of any one of the above embodiments, which comprises at least one of the following alterations:
(i) 31C, 46C, 52C, 59C, 91C, 99C, 100C, 141C, 162C, 176C, 177C, 199C, and/or 247C, preferably 52C, 99C, 141C, and/or 199C;
(ii) 4P, 5P, 41P, 91P, 111P, 136P, 137P, 154P, 161P, 240P, 282P, 283P, 284P, 289P, and/or 355P, preferably 4P, 5P, 111P;
(iii) 52E, 55D,I, 57Y, 76G, 84Y, 104A, 105F, 107D,G, 109A, G, 121T, 273L,Q, 285G,R, 286Q, 294T, 299L, 331K, 351Y, and/or 362K, preferably 57Y, 76G, 107G, 273L, 286Q and/or 362K;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24), preferably KEKKV (SEQ ID NO: 23);
(vi) 119K,R, and/or 411K,R, preferably 119K;
(vii) 107E, and/or 164D,E;
(viii) 46D,E, 82E, 223E, 276K,R, 362K,R, 379K,R, 385D, 409D,E, and/or 410D,E preferably 46E, 223E 362K,R, and/or 379K,R;
(ix) 53V,Q, 121D, 167Q, 196Q, 200K,R, 202N, 218Q, 239Q, 241Q, 285N, 314G,N, 324N, and/or 406A, preferably 53V, 121D, 196Q, 200K, 202N, 218Q, 241Q, 314N, and/or 406A;
(x) 114H,N,T 115Q, 116A,E,P,T,Q, 117D,E,K, 118I,L,M,T 119G,K,S, 120K,S,T,Q, 121A,M,P,T,V, 122D, 123P,S, and/or 124L,T,V preferably 114T 115Q, 116A,T, 117D, 118T 119K,S, 120S, 121P, 122D, 123P, and/or 124L;
(xi) 31T, 74A, 171T, 203T, 281H, 308A, and/or 316D; and/or
(xii) 339D.

d). The phytase of any one of the above embodiments, which has improved properties.

e). The phytase of embodiment c) or c1), which comprises at least one of the one or more alterations of features (i), (ii), (iii), (iv), (v), (vi), (vii), (viii), (x), (xi) and/or (xii) of embodiment 3 and has an improved thermostability.

f). The phytase of embodiment c) or c1), which comprises at least one of the one or more alterations of features (ix) and/or (x) of embodiment c) and has an improved pH profile.

g). The phytase of embodiment c) or c1), which comprises at least one of the one or more alterations of feature (x) of embodiment c) and has an improved specific activity.

h). The phytase of embodiment c) or c1), which comprises at least one of the one or more alterations of feature (xi) of embodiment c) and has an amended glycosylation pattern.

i). The phytase of embodiment c) or c1), which comprises the alteration of feature (xii) of embodiment c) which changes a potential protease cleavage site.

j). The phytase of any one of embodiment a)-d) including a1)-a5) and c1), which comprises at least one of the following alterations:
(i) 141C/199C, 91C/46C, 52C/99C, 31C/176C, 31C/177C, 59C/100C, and/or 162C/247C;
(ii) 41P, 91P, 136P, 137P, 154P, 161P, 355P, 111P, 240P, 282P, 283P, 284P, 289P, 4P, and/or 5P;
(iii) 52E, 55I, 57Y, 104A/105F, 107D,G, 109A,G, 76G, 84Y, 121T, 362K, 273L,Q, 285G,R, 286Q, 294T, 299L, 331K/55D, and/or 351Y;
(iv) 1*, 1*/2*, or 1*/2*/3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) 119R,K, and/or 411R,K;
(vii) 107E, and/or 164E,D;
(viii) 362R,K, 276R,K, 379R,K, 409D,E, 223E, 385D, 46D,E, 410D,E, and/or 82E;
(ix) 218Q, 324N, 200R,K, 121D, 196Q, 202N, 406A, 167Q, 53V,Q, 241Q, 314N,G, 239Q, and/or 285N;
(x) 114H/115Q/116E/117K/118M/119G/120T/121M/122D/123P/124T, 114H/115Q/116Q/117D/118I/119K/120Q/121V/122D/123S/124L, 114H/115Q/116P/117E/118I/119G/120K/121M/122D/123P/124V, 114T/115Q/116A/117D/118T/119S/120S/121P/122D/123P/124L, 114H/115Q/116Q/117D/118I/119K/120Q/121A/122D/123P/124L, 114T/115Q/116T/117D/118T/119S/120S/121P/122D/123P/124L, or 114N/115Q/116N117D/118L/119K/120K/121T/122D/123P/124L;
(xi) 31T, 74A, 171T, 203T, 281H, 316D, and/or 308A; and/or
(xii) 339D.

k). The phytase of any one of embodiment a)-d) including a1)-a5) and c1), which comprises at least one of the following alterations:
(i) K141C/V199C, Q91C/W46C, G52C/A99C, N31C/E176C, N31C/T177C, G59C/F100C, and/or S162C/S247C;
(ii) D41P, Q91P, N136P, T137P, L154P, S161P, T355P, Q111P, K240P, G282P, T283P, T284P, G289P, N4P, and/or G5P;
(iii) G52E, V55I, E57Y, L104A/A105F, K107D,G, Q109A,G, T76G, A84Y, N121T, I362K, M273L,Q, E285G,R, N286Q, V294T, I299L, E331K/V55D, and/or F351Y;
(iv) E1*, E1*/E2*, or E1*/E2*/Q3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) E119R,K, and/or E411R,K;
(vii) K107E, and/or R164E,D;
(viii) I362R,K, T276R,K, I379R,K, V409D,E, Q223E, N385D, W46D,E, T410D,E, and/or Q82E;
(ix) E218Q, D324N, T200R,K, N121D, E196Q, D202N, E406A, E167Q, E53V,Q, E241Q, D314N,G, E239Q, and/or E285N;
(x) Y114H/K116E/D117K/E118M/E119G/K120T/N121M/L124T, Y114H/K116Q/E118I/E119Q/K120Q/N121V/P123S, Y114H/K116P/D117E/E118I/E119G/N121M/L124V, Y114T/K116A/E118T/E119S/K120S/N121P, Y114H/K116Q/E118I/E119K/K120Q/N121A, Y114T/K116T/E118T/E119S/K120S/N121P, or Y114N/K116A/E118L/E119K/N121T;
(xi) N31T, N74A, N171T, N203T, N281H, N316D, and/or N308A; and/or
(xii) R339D.

l). The phytase of embodiment k) which is a variant of SEQ ID NO: 2.

m). The phytase of any one of embodiment a)-d) including a1)-a5) and c1), which comprises at least one of the following alterations:
(i) T141C/V199C, Q91C/W46C, G52C/A99C, D31C/E176C, D31C/T177C, G59C/F100C, and/or S162C/S247C;
(ii) D41P, Q91P, N136P, T137P, L154P, S161P, T355P, Q111P, K240P, G282P, T283P, T284P, G289P, N4P, and/or G5P;
(iii) G52E, V55I, E57Y, L104A/A105F, K107D,G, Q109A, G, T76G, A84Y, I362K, M273L,Q, E285G,R, N286Q, V294T, I299L, E331K/V55D, and/or F351Y;
(iv) E1*, E1*/E2*, or E1*/E2*/Q3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) E119R,K, and/or E411R,K;
(vii) K107E, R164E,D;
(viii) I362R,K, T276R,K, I379R,K, V409D,E, Q223E, N385D, W46D,E, T410D,E, Q82E;

(ix) E218Q, D324N, T200R,K, T121D, E196Q, D202N, E406A, E167Q, E53V,Q, E241Q, D314N,G, E239Q, and/or E285N;
(x) Y114H/K116E/D117K/E118M/E119G/K120T/T121M/L124T, Y114H/K116Q/E118I/E119K/K120Q/T121V/P123S, Y114H/K116P/D117E/E118I/E119G/T121M/L124V, Y114T/K116A/E118T/E119S/K120S/T121P/, Y114H/K116Q/E118I/E119K/K120Q/T121A/, Y114T/K116T/E118T/E119S/K120S/T121P, or Y114N/K116A/E118L/E119K;
(xi) N74A, N171T, N203T, N281H, N316D, and/or N308A; and/or
(xii) R339D.

n). The phytase of embodiment m) which is a variant of SEQ ID NO: 4.

o). The phytase of any one of embodiment a)-d) including a1)-a5) and c1), which comprises at least one of the following alterations:
(i) K141C/V199C, Q91C/W46C, G52C/A99C, D31C/E176C, D31C/T177C, G59C/F100C, and/or S162C/S247C;
(ii) D41P, Q91P, N136P, T137P, L154P, S161P, T355P, Q111P, K240P, G282P, T283P, T284P, G289P, N4P, and/or G5P;
(iii) G52E, V55I, E57Y, L104A/A105F, K107D,G, Q109A,G, T76G, A84Y, N121T, I362K, M273L,Q, E285G,R, N286Q, V294T, I299L, E331K/V55D, and/or F351Y;
(iv) E1*, E1*/E2*, or E1*/E2*/Q3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) E119R,K, and/or E411R,K;
(vii) K107E, and/or R164E,D;
(viii) I362R,K, T276R,K, I379R,K, V409D,E, Q223E, N385D, W46D,E, T410D,E, andor Q82E;
(ix) E218Q, D324N, T200R,K, N121D, E196Q, D202N, E406A, E167Q, E53V,Q, E241Q, D314N,G, E239Q, and/or E285N;
(x) Y114H/K116E/D117K/E118M/E119G/K120T/N121M/L124T, Y114H/K116Q/E118I/E119K/K120Q/N121V/P123S, Y114H/K116P/D117E/E118I/E119G/N121M/L124V, Y114T/K116A/E118T/E119S/K120S/N121P, Y114H/K116Q/E118I/E119K/K120Q/N121A, Y114T/K116T/E118T/E119S/K120S/N121P, or Y114N/K116A/E118L/E119K/N121T;
(xi) N74A, N171T, N203T, N281H, and/or N308A; and/or
(xii) R339D.

p). The phytase of embodiment o) which is a variant of SEQ ID NO: 3.

q). The phytase of any one of embodiment a)-d) including a1)-a5) and c1), which comprises at least one of the following alterations:
(i) K141C/V199C, Q91C/W46C, G52C/A99C, N31C/E176C, N31C/T177C, G59C/F100C, and/or S162C/S247C;
(ii) D41P, Q91P, N136P, T137P, L154P, S161P, T355P, Q111P, K240P, G282P, T283P, T284P, G289P, N4P, and/or G5P;
(iii) G52E, V55I, E57Y, L104A/A105F, K107D,G, Q109A,G, T76G, A84Y, N121T, I362K, M273L,Q, E285G,R, N286Q, V294T, I299L, V55D, and/or F351Y;
(iv) E1*, E1*/E2*, or E1*/E2*/Q3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) E119R,K, and/or E411R,K;
(vii) K107E, and/or R164E,D;
(viii) I362R,K, T276R,K, I379R,K, V409D,E, Q223E, N385D, W46D,E, T410D,E, and/or Q82E;
(ix) E218Q, D324N, T200R,K, N121D, E196Q, D202N, E406A, E167Q, E53V,Q, E241Q, D314N,G, E239Q, and/or E285N;
(x) Y114H/K116E/D117K/E118M/E119G/K120T/N121M/L124T, Y114H/K116Q/E118I/E119K/K120Q/N121V/P123S, Y114H/K116P/D117E/E118I/E119G/N121M/L124V, Y114T/K116A/E118T/E119S/K120S/N121P, Y114H/K116Q/E118I/E119K/K120Q/N121A, Y114T/K116T/E118T/E119S/K120S/N121P, or Y114N/K116A/E118L/E119K/N121T;
(xi) N31T, N74A, N171T, N203T, N281H, N316D, and/or N308A; and/or
(xii) R339D.

r). The phytase of embodiment q) which is a variant of SEQ ID NO: 6.

s). The phytase of any one of embodiment a)-d) including a1)-a5) and c1), which comprises at least one of the following alterations:
(i) K141C/V199C, Q91C/W46C, G52C/A99C, D31C/E176C, D31C/T177C, G59C/F100C, and/or S162C/S247C;
(ii) D41P, Q91P, N136P, T137P, L154P, S161P, T355P, Q111P, K240P, G282P, T283P, T284P, G289P, N4P, and/or G5P;
(iii) G52E, V55I, E57Y, L104A/A105F, K107D,G, Q109A,G, T76G, A84Y, I362K, M273L,Q, E285G,R, N286Q, V294T, I299L, E331K/V55D, and/or F351Y;
(iv) E1*, E1*/E2*, or E1*/E2*/P3*;
(v) wherein K179, T180, T181, E182, K183, S184, T185, and K186 have been replaced by QADKP (SEQ ID NO: 17), GEDKP (SEQ ID NO: 18), NGISA (SEQ ID NO: 19), IAGKS (SEQ ID NO: 20), KEKHQ (SEQ ID NO: 21), KEKQQ (SEQ ID NO: 22), KEKKV (SEQ ID NO: 23), or KTDKL (SEQ ID NO: 24);
(vi) E119R,K, and/or E411R,K;
(vii) K107E, and/or R164E,D;
(viii) I362R,K, T276R,K, I379R,K, V409D,E, Q223E, N385D, W46D,E, T410D,E, and/or Q82E;
(ix) E218Q, D324N, T200R,K, T121D, E196Q, D202N, E406A, E167Q, E53V,Q, E241Q, D314N,G, E239Q, and/or E285N;
(x) Y114H/K116E/D117K/E118M/E119G/K120T/T121M/L124T, Y114H/K116Q/E118I/E119K/K120Q/T121V/P123S, Y114H/K116P/D117 E/E118I/E119G/T121M/L124V, Y114T/K116A/E118T/E119S/K120S/T121P, Y114H/K116Q/E118I/E119K/K120Q/T121A, Y114T/K116T/E118T/E119S/K120S/T121P, or Y114N/K116A/E118L/E119K;
(xi) D31T, N74A, N171T, N203T, N281H, N316D, and/or N308A; and/or
(xii) R339D.

t). The phytase of embodiment s) which is a variant of SEQ ID NO: 9.

u). An isolated nucleic acid sequence comprising a nucleic acid sequence which encodes the phytase of any of embodiment a)-t) including a1)-a5) and c1).

v). A nucleic acid construct comprising the nucleic acid sequence of embodiment u) operably linked to one or more control sequences that direct the production of the phytase in a suitable expression host.

w). A recombinant expression vector comprising the nucleic acid construct of embodiment v).

x). A recombinant host cell comprising the nucleic acid construct of embodiment v) and/or the expression vector of embodiment w).

y). A method for producing the phytase of any one of embodiment a)-t) including a1)-a5) and c1), comprising
(a) cultivating the host cell of embodiment x) to produce a supernatant comprising the phytase; and (b) recovering the phytase.

z). A transgenic plant, or plant part, capable of expressing a phytase of any one of embodiment a)-t) including a1)-a5) and c1).

ae). A transgenic, non-human animal, or products, or elements thereof, being capable of expressing a phytase of any one of embodiment a)-t) including a1)-a5) and c1).

oe). A composition comprising at least one phytase of any one of embodiment a)-t) including a1)-a5) and c1), and
(a) at least one fat soluble vitamin;
(b) at least one water soluble vitamin; and/or
(c) at least one trace mineral.

aa). The composition of embodiment oe) further comprising at least one enzyme selected from the following group of enzymes: amylase, phytase, phosphatase, xylanase, galactanase, alpha-galactosidase, protease, phospholipase, and/or beta-glucanase.

bb). The composition of any one of embodiment oe)-aa) which is an animal feed additive. cc). An animal feed composition having a crude protein content of 50 to 800 g/kg and comprising the phytase of any one of embodiment a)-t) including a1)-a5) and c1) or the composition of any one of embodiment oe)-aa).

dd). A method for improving the nutritional value of an animal feed, wherein the phytase of any one of embodiment a)-t) including a1)-a5) and c1) or the composition of any one of embodiment oe)-aa) is added to the feed.

ee). A process for reducing phytate levels in animal manure comprising feeding an animal with an effective amount of the feed of embodiment cc).

ff). A method for the treatment of vegetable proteins, comprising the step of adding the phytase of any one of embodiment a)-t) including a1)-a5) and c1) or the composition of any one of embodiment oe)-aa) to at least one vegetable protein or protein source.

gg). Use of the phytase of any one of embodiment a)-t) including a1)-a5) and c1) or the composition of any one of embodiment oe)-aa) in animal feed; in the preparation of animal feed; for improving the nutritional value of animal feed; for reducing phytate levels in animal manure; for the treatment of vegetable proteins; or for liberating phosphorous from a phytase substrate.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used were commercial products of at least reagent grade.

Example 1

Preparation of Variants, and Test of Thermostability and pH Profile

Preparation of Phytase Variants

DNA encoding a variant of the phytase having the amino acid sequence of SEQ ID NO: 2 is generated by methods known in the art, and the constructs are fused by PCR to the DNA coding for the signal peptide described by Takami et al in Biosci. Biotechnol. Biochem. 56:1455 (1992) and integrated by homologous recombination into the genome of a *Bacillus subtilis* host cell (see Diderichsen et al (1990), J. Bacteriol., 172, 4315-4321) using standard techniques. The genes are expressed under the control of a triple promoter system (as described in WO 99/43835) and the resulting phytase proteins purified using conventional methods.

Determination of Temperature Stability

The temperature stability of a phytase variant may be determined in the following way: 500 microliter protein solution of the variant and of the reference protein (SEQ ID NO: 2, SEQ ID NO: 3, SEQ ID NO: 4, and/or SEQ ID NO: 6) having approximately 10 microgram protein per ml, and being dissolved in 0.1 M Na-acetate buffer, pH 5.5, are split in two portions, one portion is incubated at a desired elevated temperature (e.g. 50° C., 55° C., 60° C., 65° C., 70° C., 75° C., 80° C., or 85° C.) in plastic containers, the other is stored at 5° C. After 30 minutes incubation at the elevated temperature the protein solutions are transferred to an ice-bath and the activity of the cooled as well as the heated sample is measured by the phosphatase assay described below (buffer blind subtracted). The residual activity is defined as the activity after heat-treatment divided by the activity of the cooled sample (in %). A variant is considered to be more temperature stable (thermostable) if the residual activity in the phosphatase, or phytase, assay is higher, as compared to the reference.

Determination of Phosphatase Activity 75 microliter phytase-containing enzyme solution is dispensed in a microtiter plate well, e.g. NUNC 269620 and 75 microliter substrate is added (for preparing the substrate, two 5 mg p-nitrophenyl phosphate tablets (Sigma, Cat.No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer. One phosphatase unit is defined as the enzyme activity that releases 1 micromol phosphate/min under the given reaction conditions (buffer blind subtracted). The absorbance of 1 micromol p-nitrophenol is determined to be 56 AU (AU=absorbancy units) under assay conditions.

DSC Measurements

Differential Scanning calorimetry (DSC) may be performed at various pH-values using the VP-DSC from Micro Cal. Scans are performed at a constant scan rate of 1.5° C./min from 20-90° C. Before running the DSC, the phytases are desalted using NAP-5 columns (Pharmacia) equilibrated in the appropriate buffers (e.g. 0.1 M glycine-HCl, pH 2.5 or 3.0; 20 mM sodium acetate pH 4.0; 0.1 M sodium acetate, pH 5.5; 0.1 M Tris-HCl, pH 7.0). Data-handling is performed using the MicroCal Origin software (version 4.10), and the denaturation temperature, Td (also called the melting temperature, Tm) is defined as the temperature at the apex of the peak in the thermogram.

Amended pH Profile: Determination of pH 3.5/5.5 Activity Ratio

An amendment of the pH profile of a phytase variant may be determined as follows: The activity is measured at pH 3.5 (0.1 M acetate buffer, pH 3.5) and at pH 5.5 (0.1 M acetate buffer, pH 5.5), in both cases the buffer blind is subtracted. The activity determined at pH 3.5 is divided by the activity determined at pH 5.5, i.e. the two absorbancy measurements are divided (see below). To measure the activity, supernatants of the variants and references are appropriately diluted (e.g. 1:5000) in the respective buffer. 75 microliter of the respective enzyme solution is dispensed in a microtiter plate well, e.g. NUNC 269620 and 75 microliter substrate with the corresponding pH is added (the substrate is prepared by dissolving two 5 mg p-nitrophenyl phosphate tablets (Sigma, Cat.No. N-9389) in 10 ml 0.1 M Na-acetate buffer, pH 5.5 and 10 ml 0.1 M acetate buffer, pH 3.5, respectively). The plate is sealed and incubated 15 min., shaken with 750 rpm at 37° C. After the incubation time 75 microliter stop (0.1 M di-sodiumtetraborate in water) reagent is added and the absorbance at 405 nm is measured in a microtiter plate spectrophotometer.

Determination of Phytase Activity 75 microliters phytase-containing enzyme solution, appropriately diluted (e.g. in 0.25M sodium acetate, 0.005% (w/v) Tween-20. pH 5.5), is dispensed in a microtiter plate well, e.g. NUNC 269620, and 75 microliter substrate is added (prepared by dissolving 100 mg sodium phytate from rice (Aldrich Cat.No. 274321) in 10 ml 0.25 M Na-acetate buffer, pH 5.5). The plate is sealed and incubated 15 min. shaken with 750 rpm at 37° C. After the incubation time 75 microliter stop reagent is added (the stop reagent being prepared by mixing 10 ml molybdate solution (10% (w/v) Ammonium heptamolybdate in 0.25% (w/v) ammonia solution); 10 ml ammonium vanadate (0.24% commercial product from Bie&Berntsen, Cat.No. LAB17650) and 21.7% (w/v) nitric acid) the absorbance at 405 nm is measured in a microtiter plate spectrophotometer. The phytase activity is expressed in the unit of FYT, one FYT being the amount of enzyme that liberates 1 micromol inorganic ortho-phosphate per min. under the conditions above. An absolute value for the measured phytase activity is obtained by reference to a standard curve prepared from appropriate dilutions of inorganic phosphate or to a standard curve made from dilutions of a phytase enzyme preparation with known activity (such standard enzyme preparation with a known activity is available on request from Novozymes A/S, Krogshoejvej 36, DK-2880 Bagsvaerd).

Example 2

Influence of Expression Host/Glycosylation on Thermostability

Expression in Bacillus

The phytase of SEQ ID NO: 2 was expressed in *Bacillus subtilis* as described in Example 1, and purified using conventional methods: Centrifugation, germ filtration, ammonium sulphate precipitation (80% ammonium sulphate saturation), centrifugation, re-suspension of pellets in buffer A (50 mM sodium acetate, 1.5 M ammonium sulphate pH 4.5), filtration, hydrophobic interaction chromatography (Phenyl Toyopearl, loading with buffer A, eluting with buffer B (50 mM sodium acetate pH 4.5)), and cation exchange chromatography (SP-sepharose, loading with 10 mM sodium citrate pH 4.0, eluting with a linear salt gradient (10 mM sodium citrate pH 4.0+1 M NaCl).

Expression in *Pichia*

Still further, the phytase of SEQ ID NO: 2 was expressed in *Pichia pastoris* as generally described by Rodriguez et al in Archives of Biochemistry and Biophysics, vol. 382, no. 1, 2000, pp. 105-112. The phytase was purified from the supernatant of the fermentation broth as follows: Precipitation with ammonium sulfate (80% saturation), re-dissolution in 10 ml 25 mM sodium acetate buffer pH4.5, dialysis against the same buffer, and filtration through a 0.45 mm filter. 150 ml of this solution was applied to a 40 ml SP Sepharose FF column (Pharmacia) equilibrated with the same buffer pH 4.5, and the protein was eluted with a linear NaCl gradient (0-0.5M). Fractions from the column were analyzed for phytase activity. Fractions with phytase activity were checked by SDS-PAGE and the pure fractions were pooled. The protein concentration was measured by using BCA kit (Pierce).

Thermostability by DSC

The *Pichia*- and the *Bacillus*-expressed phytase of SEQ ID NO: 2 were subjected to thermostability measurements by Differential Scanning calorimetry (DSC).

Sample Preparation:

Samples (less than 3 ml in volume) were dialyzed in a cold room (approx. 5 degrees centigrade) for a minimum of 1 hour against 500 ml of 20 mM sodium acetate buffer pH 4.0. The sample was transferred to 500 ml of fresh, cold buffer preparation and left to dialyze overnight. The samples were filtered using a 0.45 micrometer syringe filter, volume adjusted to approx. 1.5 ml using the dialysis buffer, and $A_{280}$ (absorbancy at 280 nm) recorded. The dialysis buffer was used as reference in the DSC scans. The samples were degassed using vacuum suction and stirring for approx. 10 minutes.

During sample preparation of the *Pichia*-expressed phytase (dialysis against 20 mM sodium acetate (NaAc) pH 4.0) a precipitate was formed. The supernatant was used for a first experiment. Afterwards the remaining part of the purified stock solution was dialysed against 20 mM NaAc pH 4.0 and this allowed precipitation of some low Mw impurities present in the batch. This batch was used for a second experiment which revealed a Tm very similar to the first experiment (54 vs. 55° C.).

DSC Experiment:

Experimental settings using a MicroCal™ VP-DSC instrument: Scan rate: 90 K/h. Scan interval: 20-90 degrees centigrade. Feedback mode: None. Filtering period: 16 s.

The enzyme concentrations of the samples were approx. 1-1.5 mg/ml as estimated by $A_{280}$ and a theoretically calculated extinction coefficient at 280 nm (Vector NTI version 9.0.0). The thermal unfolding temperature (Td) was evaluated using MicroCal Origin software (version 4.10) and the denaturation temperature determined as the temperature at the apex in the thermogram.

The results are summarized in Table 2 below.

TABLE 2

| Host cell | Buffer | Scanrate (° C./h) | Scan interval (° C.) | $T_d$ (° C.) | $A_{280}$ |
|---|---|---|---|---|---|
| B. subtilis | 20 mM NaAc pH 4.0 | 90 | 20-90 | 62 | 1.6 |
| P. pastoris | 20 mM NaAc pH 4.0 | 90 | 20-90 | 55 | 1.9 |

From Table 2 it clearly appears that the *Pichia*-expressed phytase is much less thermostable than the *Bacillus*-expressed phytase.

The *Pichia*-expressed phytase was heavily glycosylated, as visualized by a broad range of molecular masses using mass spectrometry (Maldi-TOF), whereas the *Bacillus*-expressed phytase was not glycosylated.

Example 3

Phytase Variant R339D

A protein-engineered variant of the phytase of SEQ ID NO: 2 having the substitution R339D was prepared and expressed in *Aspergillus oryzae* using methods known in the art. Its denaturation temperature, Td, was determined to 62.5° C. (20 mM sodium acetate, pH 4.0), using DSC as described in Example 2.

The R339D substitution furthermore serves to remove a Kex2 protease cleavage site of potential relevance for expression in *Aspergillus*.

Example 4

Animal Feed and Animal Feed Additives Comprising a Phytase Variant

Animal Feed Additive

A formulation of phytase variant R339D of SEQ ID NO: 2 containing 0.15 g phytase enzyme protein is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8% | | Calcium |
| 25% | | Sodium |

Animal Feed

This is an example of an animal feed (broiler feed) comprising 1.5 mg/kg (1.5 ppm) of phytase variant R339D of SEQ ID NO: 2 (calculated as phytase enzyme protein):
62.55% Maize
33.8% Soybean meal (50% crude protein, CP)
1.0% Soybean oil
0.2% DL-Methionine
0.22% DCP (dicalcium phosphate)
0.76% CaCO$_3$ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Example 5

Determination of Temperature Stability

Eight variants of SEQ ID NO: 2 (the alterations as compared to SEQ ID NO: 2 are shown in Table 3 below) were prepared as described in Example 1. The two reference phytases having SEQ ID NO: 2 and SEQ ID NO: 3 were prepared in the same manner.

The temperature stability was determined as follows:
200 microliter supernatants of each of the variants and the reference proteins were split in two portions, one portion was incubated at 50° C. in plastic containers, the other was stored at 5° C. After 30 minutes incubation at 50° C. the protein solutions were transferred to an ice-bath. After dilution 1:100 in 0.1 M Na-acetate buffer, pH 5.5 the activity of the cooled and heated sample was measured by the phosphatase assay of Example 1 ("Determination of phosphatase activity"), buffer blind subtracted. The results are shown in Table 3 below as enzyme activity (in absorption units (AU)) after incubation for 30 minutes at 5° C. and 50° C., respectively, and the residual activity (RA) is calculated as activity of the heat-treated sample (50° C. incubation) divided by the activity of the cooled sample (5° C. incubation), in %.

TABLE 3

Phytase variants with improved thermostability

| Phytase | 5° C. (AU) | 50° C. (AU) | RA (%) |
|---|---|---|---|
| SEQ ID NO: 2 | 0.210 | 0.070 | 33 |
| SEQ ID NO: 3 | 1.052 | 0.027 | 3 |
| N4P of SEQ ID NO: 2 | 0.513 | 0.313 | 61 |
| G5P of SEQ ID NO: 2 | 0.576 | 0.287 | 50 |
| Q111P of SEQ ID NO: 2 | 1.053 | 0.577 | 55 |
| E1* of SEQ ID NO: 2 | 0.909 | 0.401 | 44 |
| E1*/E2* of SEQ ID NO: 2 | 0.322 | 0.159 | 50 |
| E1*/E2*/Q3* of SEQ ID NO: 2 | 0.101 | 0.051 | 51 |
| M273L of SEQ ID NO: 2 | 1.599 | 0.897 | 56 |
| N286Q of SEQ ID NO: 2 | 0.062 | 0.024 | 39 |

Example 6

Performance in Animal Feed in an in vitro Model

The performance in animal feed of a phytase variant is compared, in an in vitro model, to the performance of a reference protein such as SEQ ID NO: 2, SEQ ID NO: 3, SEQ ID NO: 4, and/or SEQ ID NO: 6. The in vitro model simulates gastro-intestinal conditions in a monogastric animal and correlates well with results obtained in animal trials in vivo. The comparison is performed as follows:

Phytase activity in the variant sample is determined as described in Example 1 under "Determination of phytase activity".

Feed samples composed of 30% soybean meal and 70% maize meal with added CaCl$_2$ to a concentration of 5 g calcium per kg feed are then prepared and pre-incubated at 40° C. and pH 3.0 for 30 minutes followed by addition of pepsin (3000 U/g feed) and suitable dosages of the phytases (identical dosages are used for all phytases to be tested to allow comparison), for example between 0.25 to 0.75 phytase units FYT/g feed. A blank with no phytase activity is also included as reference. The samples are then incubated at 40° C. and pH 3.0 for 60 minutes followed by pH 4.0 for 30 minutes.

The reactions are stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates are separated by high performance ion chromatography as described by Chen et al in Journal of Chromatography A (2003) vol. 1018, pp. 41-52 and quantified as described by Skoglund et al in J. Agric. Food Chem. (1997), vol. 45, pp. 431-436.

Released phosphorous is then calculated as the difference in inositol-phosphate bound phosphorous (IP-P) between phytase-treated and non-treated samples. The relative performance of the variant is calculated as the percentage of the phosphorous released by the reference phytase.

The in vitro performance of a number of phytase variants of SEQ ID NO: 2 was determined as described above, in a dosage of 125 FYT/kg feed.

The results are shown in Tables 4A and 4B below, for supernatants and purified phytases, respectively. Residual IP6-P designates the amount of IP6-P (phytate phosphorous) left after the in vitro incubation and it is indicated in mg/g DM (Dry Matter). Degraded IP6-P is determined as the difference between residual IP6-P of the blank and residual IP6-P of the respective sample. Finally, in the last column degraded IP6-P is indicated relative to the phytase having SEQ ID NO: 2. In Table 4A the blank and the reference (SEQ ID NO: 2) values are averages from a number of independent determinations, whereas the other values are based on single determinations. In Table 4B the blank value is average from a number of independent determinations, wheres the other values are based on single determinations.

TABLE 4A

In vitro performance of phytase variant supernatants

| Variant No./(amendment as compared to SEQ ID NO: 2) | Residual IP6-P mg/g DM | Degraded IP6-P mg/g DM | Degraded IP6-P (%) |
|---|---|---|---|
| Blank | 2.462 | | |
| 026 (SEQ ID NO: 3) | 0.106 | 2.356 | 99 |
| 000 (SEQ ID NO: 2) | 0.071 | 2.391 | 100 |
| 008 (G52C/A99C) | 0.387 | 2.075 | 87 |
| 009 (G59C/F100C) | 0.272 | 2.190 | 92 |
| 010 (K141C/V199C) | 0.207 | 2.255 | 94 |
| 015 (N4P) | 0.064 | 2.387 | 100 |
| 016 (G5P) | 0.099 | 2.351 | 98 |
| 018 (Q111P) | 0.100 | 2.350 | 98 |
| 020 (T137P) | 0.370 | 2.092 | 87 |
| 021 (L154P) | 0.382 | 2.080 | 87 |
| 022 (S161P) | 0.235 | 2.227 | 93 |
| 023 (K240P) | 0.581 | 1.881 | 79 |
| 024 (T355P) | 0.744 | 1.718 | 72 |
| 028 (G52E) | 0.716 | 1.746 | 73 |
| 030 (E57Y) | 0.666 | 1.796 | 75 |
| 032 (A84Y) | 0.667 | 1.795 | 75 |
| 034 (L104A) | 0.709 | 1.753 | 73 |
| 035 (A105E) | 0.553 | 1.908 | 80 |
| 036 (K107D) | 0.767 | 1.695 | 71 |
| 037 (K107G) | 0.450 | 2.012 | 84 |
| 040 (E1*) | 0.069 | 2.381 | 100 |
| 041 (E1*/E2*) | 0.095 | 2.367 | 99 |
| 042 (E1*/E2*/Q3*) | 0.084 | 2.366 | 99 |
| 043 (N121T) | 0.423 | 2.039 | 85 |
| 044 (M273L) | 0.107 | 2.355 | 98 |
| 048 (E285G) | 0.553 | 1.909 | 80 |
| 050 (N286Q) | 0.068 | 2.382 | 100 |
| 051 (G289P) | 0.560 | 1.902 | 80 |
| 052 (V294T) | 0.746 | 1.716 | 72 |
| 053 (I299L) | 0.848 | 1.614 | 67 |
| 056 (I362K) | 0.699 | 1.763 | 74 |
| 059 (K107E) | 0.537 | 1.925 | 80 |

Variants 015, 016, 018, 040, 041, 042, 044, and 050 appear to have an in vitro performance which is at least as good or better than the phytases of SEQ ID NO: 2 and 3.

TABLE 4B

In vitro performance of purified phytase variants

| Variant No./(amendment as compared to SEQ ID NO: 2) | Residual IP6-P mg/g DM | Degraded IP6-P mg/g DM | Degraded IP6-P (%) |
|---|---|---|---|
| Blank | 2.412 | | |
| 026 (SEQ ID NO: 3) | 0.630 | 1.782 | 112 |
| 102 (SEQ ID NO: 4) | 0.717 | 1.695 | 106 |
| 000 (SEQ ID NO: 2) | 0.816 | 1.596 | 100 |
| 101 (SEQ ID NO: 9) | 0.631 | 1.781 | 112 |
| 018 (Q111P) | 0.843 | 1.569 | 98 |
| 030 (E57Y) | 0.318 | 2.094 | 131 |
| 031 (T76G) | 0.384 | 2.028 | 127 |
| 037 (K107G) | 0.657 | 1.755 | 110 |
| 041 (E1*/E2*) | 0.858 | 1.553 | 97 |
| 044 (M273L) | 0.943 | 1.469 | 92 |
| 050 (N286Q) | 0.865 | 1.546 | 97 |
| 056 (I362K) | 0.425 | 1.987 | 125 |
| 072 (I362R) | 0.430 | 1.982 | 124 |
| 085 (N121D) | 0.555 | 1.856 | 116 |
| 087 (E196Q) | 0.547 | 1.865 | 117 |
| 089 (T200K) | 0.405 | 2.007 | 126 |
| 090 (D202N) | 0.586 | 1.826 | 114 |
| 091 (E218Q) | 1.264 | 1.148 | 72 |
| 095 (D314N) | 0.696 | 1.716 | 107 |
| 098 (E406A) | 0.515 | 1.897 | 119 |
| 125 (Y114T/Q115Q/K116A/D117D/ E118T/E119S/-K120S/N121P/ D122D/P123P/L124L) | 0.753 | 1.658 | 104 |
| 127 (Y114T/Q115Q/K116T/D117D/ E118T/E119S/-K120S/N121P/ D122D/P123P/L124L) | 0.861 | 1.550 | 97 |

Variants 030, 031, 037, 056, 072, 085, 087, 089, 090, 095, 098, and 125 appear to perform at least as good in vitro as the phytase of SEQ ID NO: 3.

Example 7

Specific Activity

The specific activity of a phytase variant is determined on highly purified samples dialysed against 250 mM sodium acetate, pH 5.5. The purity is checked beforehand on an SDS poly acryl amide gel showing the presence of only one component.

The protein concentration is determined by amino acid analysis as follows: An aliquot of the sample is hydrolyzed in 6N HCl, 0.1% phenol for 16 h at 110° C. in an evacuated glass tube.

The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity is determined in the units of FYT as described in Example 1 ("Determination of phytase activity"), and the specific activity is calculated as the phytase activity measured in FYT units per mg phytase variant enzyme protein.

The specific activity for the phytase of SEQ ID NO: 2 and variant 072 (I362R of SEQ ID NO: 2) was determined as described above. The specific activity of variant 072 was 86% of the specific activity of the phytase of SEQ ID NO: 2. The uncertainty (standard deviation) is estimated to approximately 10%, which is mainly due to the phytase activity assay based on a complex substrate.

Example 8

Temperature Stability

A number of variants of SEQ ID NO: 2 were prepared as described in Example 1, and the *Bacillus subtilis* host strains grown in 100 ml PS1 medium (100 g/L sucrose, 40 g/L Soy flakes, 10 g/L Na$_2$HPO$_4$.12H$_2$O, 0.1 ml/L Dowfax 63N10 (Dow)) in 500 ml shake flasks for four days at 30° C. at 300 rpm.

Two reference phytases were prepared in the same manner, viz. the phytase having SEQ ID NO: 3 (corresponding to variant N31D/Q139K/L197F/N316K of SEQ ID NO: 2), and the phytase having SEQ ID NO: 4 (corresponding to variant N31D/N121T/K132T/Q139K of SEQ ID NO: 2).

Also the phytase having SEQ ID NO: 9 was included for comparison (corresponding to variant Q3P/N31D/N121T/K132T/Q139K of SEQ ID NO: 2).

The temperature stability of the variants and the reference phytases was determined as follows:

The supernatants were diluted ten times by adding 20 ul (microliter) supernatant to 180 ul 0.1M Na-acetate buffer, pH5.5+0.005% Tween-20. The diluted enzymes were split in two portions, one portion was incubated at 60° C. in plastic containers, and the other portion was stored at 5° C. After 30 minutes incubation at 60° C. the protein solutions were transferred to an ice-bath. After dilution 1:10 in 0.1M Na-acetate buffer, pH5.5, and 0.005% Tween-20, the activity of the cooled and heated sample was measured by the phosphatase assay of Example 1 ("Determination of phosphatase activity"), buffer blind subtracted.

Table 5 is a list of variants with improved temperature stability as compared to the reference phytases. For each variant, the table also specifies the alterations as compared to SEQ ID NO: 2. The enzyme activity (in absorption units (AU)) after incubation for 30 minutes at 5° C. and 60° C., respectively, was determined, and the residual activity (RA) calculated as the activity of the heat-treated sample (60° C. incubation) divided by the activity of the cooled sample (5° C. incubation). Next, the residual activity results were normalized to the residual activity of the phytase of SEQ ID NO: 2, having been expressed and treated in the same manner. The resulting Improvement Factor (IF) is shown in Table 5. For the phytase of SEQ ID NO: 2 the IF is 1.0, whereas the two reference phytases of SEQ ID NO: 3 and 4 were less thermostable than the phytase of SEQ ID NO: 2, which is apparent from the fact that the IF for these two phytases was only 0.1 and 0.3, respectively.

TABLE 5

Phytase variants with improved thermostability

| No. | Mutation | IF |
| --- | --- | --- |
| 026 | N31D/Q139K/L197F/N316K (SEQ ID NO: 3) | 0.1 |
| 101 | Q3P/N31D/N121T/K132T/Q139K (amino acids 23-433 of SEQ ID NO: 9) | 0.3 |
| 102 | N31D/N121T/K132T/Q139K (SEQ ID NO: 4) | 0.3 |
| 078 | V409E | 0.3 |
| 019 | N136P | 0.3 |
| 082 | E411K | 0.4 |
| 058 | E331K/V55D | 0.4 |
| 086 | E167Q | 0.4 |
| 110 | K179K/T180T/T181D/E182K/K183L/S184*/T185*/K186* | 0.4 |
| 059 | K107E | 0.4 |
| 087 | E196Q | 0.5 |
| 070 | T276R | 0.5 |
| 048 | E285G | 0.5 |
| 053 | I299L | 0.5 |
| 089 | T200K | 0.5 |
| 065 | E119R | 0.6 |
| 085 | N121D | 0.6 |
| 036 | K107D | 0.6 |
| 107 | K179K/T180E/T181K/E182H/K183Q/S184*/T185*/K186* | 0.6 |
| 095 | D314N | 0.7 |
| 022 | S161P | 0.7 |
| 079 | T410D | 0.7 |
| 004 | K141C | 0.7 |
| 108 | K179K/T180E/T181K/E182Q/K183Q/S184*/T185*/K186* | 0.7 |
| 094 | E285N | 0.7 |
| 068 | R164E | 0.8 |
| 081 | E411R | 0.8 |
| 002 | G52C | 0.8 |
| 020 | T137P | 0.8 |
| 096 | D314G | 0.8 |
| 120 | E1K | 0.9 |
| 042 | E1*/E2*/Q3* | 0.9 |
| 043 | N121T | 0.9 |
| 098 | E406A | 0.9 |
| 063 | Q82E | 0.9 |
| 038 | Q109A | 0.9 |
| 000 | SEQ ID NO: 2 | 1.0 |
| 016 | G5P | 1.0 |
| 030 | E57Y | 1.0 |
| 074 | I379R | 1.0 |
| 041 | E1*/E2* | 1.0 |
| 080 | T410E | 1.1 |
| 040 | E1* | 1.2 |
| 066 | E119K | 1.2 |
| 028 | G52E | 1.2 |
| 015 | N4P | 1.3 |
| 056 | I362K | 1.3 |
| 090 | D202N | 1.3 |
| 071 | T276K | 1.3 |
| 076 | N385D | 1.3 |
| 113 | Q111P/E241Q | 1.4 |
| 005 | S162C | 1.4 |
| 109 | K179K/T180E/T181K/E182K/K183V/S184*/T185*/K186* | 1.4 |
| 093 | E241Q | 1.4 |
| 069 | Q223E | 1.5 |
| 050 | N286Q | 1.5 |
| 037 | K107G | 1.5 |
| 125 | Y114T/Q115Q/K116A/D117D/E118T/E119S/K120S/N121P/D122D/P123P/L124L | 1.6 |
| 075 | I379K | 1.6 |
| 044 | M273L | 1.6 |
| 006 | N31C | 1.7 |
| 083 | E53V | 1.8 |
| 009 | G59C/F100C | 1.9 |
| 062 | W46E | 2.2 |
| 018 | Q111P | 2.2 |
| 127 | Y114T/Q115Q/K116T/D117D/E118T/E119S/K120S/N121P/D122D/P123P/L124L | 2.3 |
| 031 | T76G | 2.3 |
| 072 | I362R | 2.7 |
| 010 | K141C/V199C | 4.3 |
| 008 | G52C/A99C | 5.2 |

Example 9

Thermostability by DSC

A number of purified variants of SEQ ID NO: 2 were prepared as generally described in Example 1. Two reference phytases were prepared in the same manner, viz. the phytase having SEQ ID NO: 3 (corresponding to variant N31D/Q139K/L197F/N316K of SEQ ID NO: 2), and the phytase having SEQ ID NO: 4 (corresponding to variant N31D/N121T/K132T/Q139K of SEQ ID NO: 2). Also the phytase having SEQ ID NO: 9 was included for comparison (corresponding to variant Q3P/N31D/N121T/K132T/Q139K of SEQ ID NO: 2).

Aliquots of the protein samples were dialysed against 2×500 ml 20 mM Na-acetate, pH 4.0 at 4° C. in a 2-3 h step followed by an over night step. Each sample was 0.45 um filtered and diluted with buffer to approx. 2 $A_{280}$ units. The exact absorbance values measured are given in the results table. DSC was performed on a MicroCal VP-DSC at 90° C./h scan rate from 20-90° C. in 20 mM Na-acetate buffer, pH 4.0.

The resulting denaturation temperatures (Td) are shown in Table 6 below, which summarizes the results of three different experiments.

TABLE 6

Td measurements by DSC

| Phytase | $A_{280}$ | $T_d$ (° C.) | Comments |
|---|---|---|---|
| No. 102 (SEQ ID NO: 4) | 2.0 | 61.5 | |
| No. 000 (SEQ ID NO: 2) | 2.4 | 61.2 | |
| No. 101 (amino acids 23-433 of SEQ ID NO: 9) | 2.3 | 61.0 | |
| No. 031 (T76/G of SEQ ID NO: 2) | 2.0 | 61.3 | |
| No. 056 (I362K of SEQ ID NO: 2) | 2.4 | 62.1 | |
| No. 072 (I362R of SEQ ID NO: 2) | 2.4 | 61.6 | Minor precipitate |
| No. 000 (SEQ ID NO: 2) | 2.29 | 61 | |
| No. 018 (Q111P of SEQ ID NO: 2) | 1.97 | 62 | |
| YC044 (M273L of SEQ ID NO: 2) | 2.15 | 62 | |
| No. 000 (SEQ ID NO: 2, pilot fermentation) | 1.35 | 62 | |
| No. 026 (SEQ ID NO: 3) | 1.99 | 57 | Run twice with same result |

Example 10

Purification and Temperature Profile

The phytase variants and reference and comparative phytases used herein were purified as follows: The fermentation supernatant with the phytase was first centrifuged at 7200 rpm and 5° C. for one hour and filtered through a sandwich of four Whatman glass microfibre filters (2.7, 1.6, 1.2 and 0.7 micrometer). Following this the solution was sterile filtered (either through a Fast PES Bottle top filter with a 0.22 µm cut-off or through a Seitz-EKS depth filter using pressure). The solution was added solid ammonium sulfate giving a final concentration of 1.5 M and the pH was adjusted to 6.0 using 6 M HCl.

The phytase-containing solution was applied to a butyl-sepharose column, approximately 50 ml in a XK26 column, using as buffer A 25 mM bis-tris (Bis-(2-hydroxyethyl) imino-tris(hydroxymethyl)methan))+1.5 M ammonium sulfate pH6.0, and as buffer B 25 mM bis-tris pH6.0. The fractions from the column were analyzed for activity using the phosphatase assay (see Example 1, "Determination of phosphatase activity") and fractions with activity were pooled. The pooled fractions were dialyzed extensively against 10 mM sodium acetate pH 4.5. Following this the phytase-containing solution was purified by chromatography on S Sepharose, approximately 75 ml in a XK26 column, using as buffer A 50 mM sodium acetate pH4.5, and as buffer B 50 mM sodium acetate+1 M NaCl pH4.5. Again the fractions from the column were analyzed for activity and fractions with activity were pooled. Finally, the solution containing the purified phytase was concentrated using an Amicon ultra-15 filtering device with a 10 kDa cut-off membrane.

The molecular weight, as estimated from SDS-PAGE, was approximately 40 kDa for all phytases and the purity was in all cases >95%.

The temperature profile (phytase activity as a function of temperature) of the variants was determined in the temperature range of 20-90° C. essentially as described in Example 1 ("Determination of phytase activity"), however, the enzymatic reactions (100 microliters phytase-containing enzyme solution+100 microliters substrate) were performed in PCR tubes instead of microtiter plates. After a 15 minute reaction period at desired temperature the tubes were cooled to 20° C. for 20 seconds and 150 microliter of the reaction mixture was transferred to a microtiter plate. 75 microliter stop reagent was added and the absorbance at 405 nm was measured in a microtiter plate spectrophotometer. The results are summarized in Table 7 below. The numbers given for each temperature (20-90° C. in 10° C. steps) are relative activity (in %) normalized to the value at optimum.

TABLE 7

Temperature profiles

| | | Temperature (° C.) | | | | | | | |
|---|---|---|---|---|---|---|---|---|---|
| No. | Phytase | 20 | 30 | 40 | 50 | 60 | 70 | 80 | 90 |
| 026 | SEQ ID NO: 3 | 18 | 32 | 52 | 74 | 100 | 4 | 4 | −1 |
| 102 | SEQ ID NO: 4 | 22 | 37 | 55 | 79 | 100 | 17 | 10 | 4 |
| 000 | SEQ ID NO: 2 | 20 | 34 | 54 | 68 | 100 | 21 | 11 | 5 |
| 101 | Amino acids 23-433 of SEQ ID NO: 9 | 16 | 28 | 50 | 65 | 100 | 12 | 6 | −1 |
| 018 | Q111P of SEQ ID NO: 2 | 20 | 34 | 53 | 75 | 100 | 17 | 10 | 4 |
| 030 | E57Y of SEQ ID NO: 2 | 21 | 35 | 57 | 79 | 100 | 28 | 10 | 4 |
| 031 | T76G of SEQ ID NO: 2 | 20 | 34 | 55 | 77 | 100 | 23 | 10 | 4 |
| 037 | K107G of SEQ ID NO: 2 | 21 | 34 | 55 | 77 | 100 | 32 | 11 | 4 |
| 041 | E1*/E2* of SEQ ID NO: 2 | 21 | 34 | 56 | 78 | 100 | 15 | 9 | 4 |
| 044 | M273L of SEQ ID NO: 2 | 21 | 35 | 56 | 79 | 100 | 26 | 9 | 3 |
| 050 | N286Q of SEQ ID NO: 2 | 16 | 32 | 44 | 84 | 100 | 6 | −1 | −7 |
| 056 | I362K of SEQ ID NO: 2 | 20 | 35 | 54 | 78 | 100 | 25 | 9 | 3 |
| 062 | W46E of SEQ ID NO: 2 | 27 | 42 | 65 | 84 | 100 | 18 | 12 | 5 |
| 072 | I362R of SEQ ID NO: 2 | 21 | 35 | 56 | 79 | 100 | 23 | 11 | 5 |
| 083 | E53V of SEQ ID NO: 2 | 20 | 32 | 53 | 76 | 100 | 22 | 10 | 5 |
| 093 | E241Q of SEQ ID NO: 2 | 22 | 37 | 59 | 83 | 100 | 20 | 10 | 3 |

Variants 030, 031, 037, 044, 056, 062, 072, 083, and 093 have a higher relative activity at 70° C. as compared to the reference phytases 026 and 102.

Example 11 pH Profile

The pH profiles (phytase activity as a function of pH) of a number of variants and the same reference and comparative phytases as used in the previous examples were determined at 37° C. in the pH range of 2.0 to 7.5 (in 0.5 pH-unit steps) as described in Example 1 ("Determination of phytase activity"), except that a buffer cocktail (50 mM glycine, 50 mM acetic acid and 50 mM Bis-Tris was used instead of the 0.25 M sodium acetate pH 5.5 buffer. The results are summarized in Table 8 below. The numbers given for each pH (2.0-7.5) are relative activity (in %) normalized to the value at optimum.

TABLE 8 pH profiles

| No. | Phytase | pH | | | | | | | | | | | |
|---|---|---|---|---|---|---|---|---|---|---|---|---|---|
| | | 2.0 | 2.5 | 3.0 | 3.5 | 4.0 | 4.5 | 5.0 | 5.5 | 6.0 | 6.5 | 7.0 | 7.5 |
| 026 | SEQ ID NO: 3 | 30 | 62 | 87 | 99 | 100 | 95 | 84 | 65 | 40 | 14 | −1 | −2 |
| 102 | SEQ ID NO: 4 | 26 | 65 | 87 | 97 | 100 | 93 | 82 | 66 | 43 | 17 | 0 | −4 |
| 000 | SEQ ID NO: 2 | 33 | 60 | 89 | 100 | 99 | 95 | 80 | 61 | 35 | 11 | −2 | −4 |
| 101 | Amino acids 23-433 of SEQ ID NO: 9 | 37 | 65 | 87 | 97 | 100 | 93 | 80 | 65 | 42 | 19 | 2 | 0 |
| 018 | Q111P of SEQ ID NO: 2 | 27 | 61 | 89 | 97 | 100 | 90 | 75 | 57 | 32 | 10 | −2 | −4 |
| 030 | E57Y of SEQ ID NO: 2 | 35 | 60 | 86 | 97 | 100 | 92 | 79 | 60 | 36 | 13 | 1 | −3 |
| 031 | T76G of SEQ ID NO: 2 | 34 | 60 | 86 | 99 | 100 | 93 | 79 | 62 | 36 | 12 | 1 | −1 |
| 037 | K107G of SEQ ID NO: 2 | 33 | 59 | 87 | 100 | 99 | 93 | 78 | 60 | 34 | 10 | −2 | −4 |
| 041 | E1*/E2* of SEQ ID NO: 2 | 29 | 62 | 89 | 100 | 100 | 93 | 79 | 59 | 34 | 12 | 2 | 1 |
| 044 | M273L of SEQ ID NO: 2 | 31 | 63 | 87 | 100 | 99 | 94 | 81 | 62 | 36 | 12 | 0 | −1 |
| 050 | N286Q of SEQ ID NO: 2 | 29 | 59 | 87 | 100 | 97 | 89 | 77 | 56 | 36 | 12 | 1 | −2 |
| 056 | I362K of SEQ ID NO: 2 | 34 | 60 | 85 | 100 | 98 | 92 | 74 | 64 | 35 | 12 | 4 | 1 |
| 062 | W46E of SEQ ID NO: 2 | 13 | 40 | 77 | 100 | 95 | 88 | 72 | 52 | 29 | 10 | 1 | −1 |
| 072 | I362R of SEQ ID NO: 2 | 35 | 60 | 87 | 100 | 100 | 97 | 82 | 64 | 37 | 14 | 1 | −1 |
| 083 | E53V of SEQ ID NO: 2 | 22 | 61 | 88 | 99 | 100 | 94 | 80 | 61 | 35 | 9 | −6 | −5 |
| 085 | N121D of SEQ ID NO: 2 | 34 | 65 | 91 | 100 | 94 | 82 | 65 | 46 | 27 | 11 | 4 | 0 |
| 087 | E196Q of SEQ ID NO: 2 | 30 | 63 | 89 | 100 | 99 | 89 | 73 | 54 | 28 | 8 | 4 | 0 |
| 089 | T200K of SEQ ID NO: 2 | 25 | 58 | 86 | 100 | 92 | 78 | 61 | 43 | 18 | 4 | 0 | −1 |
| 090 | D202N of SEQ ID NO: 2 | 30 | 66 | 91 | 100 | 99 | 91 | 70 | 46 | 18 | 3 | −1 | −3 |
| 091 | E218Q of SEQ ID NO: 2 | 11 | 45 | 75 | 95 | 100 | 95 | 90 | 64 | 35 | 8 | −2 | −4 |
| 093 | E241Q of SEQ ID NO: 2 | 28 | 58 | 83 | 92 | 100 | 87 | 71 | 59 | 31 | 8 | −1 | −3 |
| 095 | D314N of SEQ ID NO: 2 | 26 | 60 | 87 | 100 | 98 | 94 | 75 | 58 | 33 | 11 | 2 | 0 |
| 098 | E406A of SEQ ID NO: 2 | 32 | 59 | 89 | 100 | 98 | 91 | 76 | 59 | 30 | 9 | 2 | −3 |
| 125 | Y114T/Q115Q/K116A/D117D/E118T/-E119S/K120S-/N121P/D122D/P123P/L124L of SEQ ID NO: 2 | 30 | 66 | 87 | 98 | 100 | 86 | 70 | 54 | 29 | 10 | 1 | −1 |
| 127 | Y114T/Q115Q/K116T/D117D/E118T/-E119S/K120S-/N121P/D122D/P123P/L124L of SEQ ID NO: 2 | 42 | 67 | 91 | 100 | 100 | 90 | 74 | 55 | 27 | 8 | −2 | −4 |

For YC062 and YC091 the pH curve (relative activity as a function of pH) seems to have shifted 0.5 pH unit towards higher pH.

Furthermore, while for most of the Table 8 phytases (including the reference phytases 026 and 102) the optimum is at pH3.5-pH4.0, an optimum pH of 3.5 is observed for no. 062, 085, and 089, and an optimum pH of 4.0 is observed for no. 091 and 093.

Example 12

Temperature Stability

The temperature stability of a number of purified variants and the same reference and comparative phytases as in the previous examples was determined by measuring residual phytase activity after incubation at 70° C. and pH 4.0 (0.1 M sodium acetate). The phytases were incubated and samples were withdrawn after 0, 10, 30 and 60 minutes and cooled on ice. The residual activity at pH 5.5 was determined using the method described in Example 1 ("Determination of phytase activity"). The results, normalized to the activity found at 0 minutes, are shown in Table 9 below.

TABLE 9

Temperature stability

| No. | Phytase | Temperature stability % after 60 min. |
|---|---|---|
| 026 | SEQ ID NO: 3 | 26 |
| 102 | SEQ ID NO: 4 | 30 |
| 000 | SEQ ID NO: 2 | 46 |
| 101 | Amino acids 23-433 of SEQ ID NO: 9 | 29 |
| 018 | Q111P of SEQ ID NO: 2 | 25 |

TABLE 9-continued

Temperature stability

| No. | Phytase | Temperature stability % after 60 min. |
|---|---|---|
| 044 | M273L of SEQ ID NO: 2 | 31 |
| 050 | N286Q of SEQ ID NO: 2 | 19 |
| 056 | I362K of SEQ ID NO: 2 | 26 |
| 062 | W46E of SEQ ID NO: 2 | 31 |
| 072 | I362R of SEQ ID NO: 2 | 32 |
| 083 | E53V of SEQ ID NO: 2 | 31 |
| 093 | E241Q of SEQ ID NO: 2 | 29 |

The above results indicate that Nos. 044, 062, 072, and 083 may be more stable under these conditions (70° C. and pH 4) than the reference phytases (although in this experiment a big variation was observed for No. 000).

Example 13

Calculating Percentage of Identity and Identifying Corresponding Positions

SEQ ID NO: 9 was aligned with SEQ ID NO: 2 using the Needle program from the EMBOSS package version 2.8.0. The substitution matrix used was BLOSUM62, the gap opening penalty was 10.0, and the gap extension penalty was 0.5. The resulting alignment is shown in FIG. 2.

The degree of identity between SEQ ID NO: 9 and SEQ ID NO: 2 is calculated as follows: The number of exact matches is 406 (all those with a vertical stroke). The length of the shortest sequence is 411 (SEQ ID NO: 2). The percentage of identity is 406/411×100%=98.8%.

The alignment of FIG. 2 is also used for deriving corresponding positions as follows: Amino acids on top of each other in this alignment are in corresponding positions. E.g. amino acid Q in position 3 of SEQ ID NO: 2 corresponds to amino acid P in position number 25 of SEQ ID NO: 9. For the present purposes we refer to the position number of SEQ ID NO: 2. Therefore, SEQ ID NO: 9 may be considered a variant of SEQ ID NO: 2 which comprises the substitution Q3P.

Other differences in the form of substitutions within the overlap of the alignment are found in positions 31, 121, 132, and 139, viz. N31D, N121T, K132T, and Q139K.

Additional differences are found in the N-terminus, where SEQ ID NO: 9 has an extension of 22 amino acids as compared to SEQ ID NO: 2.

Overall, SEQ ID NO: 9 may therefore be considered the following variant of SEQ ID NO: 2:*0aM/*0bS/*0cT/*0dF/ *0e1/*0fl/*0gR/*0hL/*0iL/*0jF/*0kF/*0mS/*0nL/*0oL/*0pC/*0qG/*0rS/*0sF/* 0tS/*0ul/*0vH/*0wA/Q3P/N31D/N121T/K132T/Q139K.

The invention claimed is:

1. A phytase variant, comprising an amino acid substitution at a position corresponding to a position in SEQ ID NO: 2 selected from the group consisting of 196, 200, and 406, wherein the variant has at least 80% identity to SEQ ID NO: 2 and has phytase activity.

2. The phytase variant of claim 1, which has at least 85% identity to SEQ ID NO: 2.

3. The phytase variant of claim 1, which has at least 90% identity to SEQ ID NO: 2.

4. The phytase variant of claim 1, which has at least 95% identity to SEQ ID NO: 2.

5. The phytase variant of claim 4, which further comprises an amino acid substitution at a position corresponding to position 57 in SEQ ID NO: 2.

6. The phytase variant of claim 5, which comprises E57Y.

7. The phytase variant of claim 4, which further comprises an amino acid substitution at a position corresponding to position 76 in SEQ ID NO: 2.

8. The phytase variant of claim 7, which comprises T76G.

9. The phytase variant of claim 4, which comprises an amino acid substitution at a position corresponding to position 196 in SEQ ID NO: 2.

10. The phytase variant of claim 9, which comprises E196Q.

11. The phytase variant of claim 4, which comprises an amino acid substitution at a position corresponding to position 200 in SEQ ID NO: 2.

12. The phytase variant of claim 11, which comprises T200K,R.

13. The phytase variant of claim 4, which comprises an amino acid substitution at a position corresponding to position 406 in SEQ ID NO: 2.

14. The phytase variant of claim 11, which comprises E406A.

15. A composition comprising the phytase variant of claim 1, and at least one of
(a) at least one fat soluble vitamin;
(b) at least one water soluble vitamin; and
(c) at least one trace mineral.

16. A composition comprising the phytase variant of claim 6, and at least one of
(a) at least one fat soluble vitamin;
(b) at least one water soluble vitamin; and
(c) at least one trace mineral.

17. A composition comprising the phytase variant of claim 8, and at least one of
(a) at least one fat soluble vitamin;
(b) at least one water soluble vitamin; and
(c) at least one trace mineral.

18. A composition comprising the phytase variant of claim 10, and at least one of
(a) at least one fat soluble vitamin;
(b) at least one water soluble vitamin; and
(c) at least one trace mineral.

19. A composition comprising the phytase variant of claim 12, and at least one of
(a) at least one fat soluble vitamin;
(b) at least one water soluble vitamin; and
(c) at least one trace mineral.

20. A composition comprising the phytase variant of claim 14, and at least one of
(a) at least one fat soluble vitamin;
(b) at least one water soluble vitamin; and
(c) at least one trace mineral.

21. The composition of claim 15, further comprising at least one enzyme selected from the following group of enzymes: amylase, phytase, phosphatase, xylanase, galactanase, alpha-galactosidase, protease, phospholipase, and/or beta-glucanase.

22. An animal feed composition having a crude protein content of 50 to 800 g/kg and comprising the phytase variant of claim 1.

23. A method for improving the nutritional value of an animal feed, wherein the phytase variant of claim 1 is added to the feed.

24. A process for reducing phytate levels in animal manure comprising feeding an animal with an effective amount of the feed composition of claim 22.

25. A phytase variant comprising an amino acid substitution at position corresponding to position 57 in SEQ ID NO: 2, wherein the substitution is E57Y and wherein the variant has at least 95% identity to SEQ ID NO: 2 and has phytase activity.

26. A comprising the phytase variant of claim 25, and at least one of
(a) at least one fat soluble vitamin;
(b) at least one water soluble vitamin; and
(c) at least one trace mineral.

27. The composition of claim 26, further comprising at least one enzyme selected from the following group of enzymes: amylase, phytase, phosphatase, xylanase, galactanase, alpha-galactosidase, protease, phospholipase, and/or beta-glucanase.

28. An animal feed composition having a crude protein content of 50 to 800 g/kg and comprising the phytase variant of claim 25.

29. A method for improving the nutritional value of an animal feed, wherein the phytase variant of claim 25 is added to the feed.

30. A process for reducing phytate levels in animal manure comprising feeding an animal with an effective amount of the feed composition of claim 28.

* * * * *

```
                            SEQUENCE LISTING

<160> NUMBER OF SEQ ID NOS: 34

<210> SEQ ID NO 1
<211> LENGTH: 1233
<212> TYPE: DNA
<213> ORGANISM: Citrobacter braakii ATCC 51113
<220> FEATURE:
<221> NAME/KEY: mat_peptide
<222> LOCATION: (1)..(1233)
<220> FEATURE:
<221> NAME/KEY: CDS
<222> LOCATION: (1)..(1233)

<400> SEQUENCE: 1 gaa gag cag aat ggt atg aaa ctt gag cgg gtt gtg ata gtg agt cgt       48
Glu Glu Gln Asn Gly Met Lys Leu Glu Arg Val Val Ile Val Ser Arg
1               5                   10                  15 cat gga gta aga gca cct acg aag ttc act cca ata atg aaa aat gtc       96
His Gly Val Arg Ala Pro Thr Lys Phe Thr Pro Ile Met Lys Asn Val
            20                  25                  30 aca ccc gat caa tgg cca caa tgg gat gtg ccg tta gga tgg cta acg      144
Thr Pro Asp Gln Trp Pro Gln Trp Asp Val Pro Leu Gly Trp Leu Thr
        35                  40                  45 cct cgt ggg gga gaa ctt gtt tct gaa tta ggt cag tat caa cgt tta      192
Pro Arg Gly Gly Glu Leu Val Ser Glu Leu Gly Gln Tyr Gln Arg Leu
    50                  55                  60 tgg ttc acg agc aaa ggt ctg ttg aat aat caa acg tgc cca tct cca      240
Trp Phe Thr Ser Lys Gly Leu Leu Asn Asn Gln Thr Cys Pro Ser Pro
65                  70                  75                  80 ggg cag gtt gct gtt att gca gac acg gat caa cgc acc cgt aaa acg      288
Gly Gln Val Ala Val Ile Ala Asp Thr Asp Gln Arg Thr Arg Lys Thr
                85                  90                  95 ggt gag gcg ttt ctg gct ggg tta gca cca aaa tgt caa att caa gtg      336
Gly Glu Ala Phe Leu Ala Gly Leu Ala Pro Lys Cys Gln Ile Gln Val
            100                 105                 110 cat tat cag aag gat gaa gaa aaa aat gat cct ctt ttt aat ccg gta      384
His Tyr Gln Lys Asp Glu Glu Lys Asn Asp Pro Leu Phe Asn Pro Val
        115                 120                 125 aaa atg ggg aaa tgt tcg ttt aac aca ttg cag gtt aaa aac gct att      432
Lys Met Gly Lys Cys Ser Phe Asn Thr Leu Gln Val Lys Asn Ala Ile
    130                 135                 140 ctg gaa cgg gcc gga gga aat att gaa ctg tat acc caa cgc tat caa      480
Leu Glu Arg Ala Gly Gly Asn Ile Glu Leu Tyr Thr Gln Arg Tyr Gln
145                 150                 155                 160 tct tca ttt cgg acc ctg gaa aat gtt tta aat ttc tca caa tcg gag      528
Ser Ser Phe Arg Thr Leu Glu Asn Val Leu Asn Phe Ser Gln Ser Glu
                165                 170                 175 aca tgt aag act aca gaa aag tct acg aaa tgc aca tta cca gag gct      576
Thr Cys Lys Thr Thr Glu Lys Ser Thr Lys Cys Thr Leu Pro Glu Ala
            180                 185                 190 tta ccg tct gaa ctt aag gta act cct gac aat gta tca tta cct ggt      624
Leu Pro Ser Glu Leu Lys Val Thr Pro Asp Asn Val Ser Leu Pro Gly
        195                 200                 205
```

```
gcc tgg agt ctt tct tcc acg ctg act gag ata ttt ctg ttg caa gag     672
Ala Trp Ser Leu Ser Ser Thr Leu Thr Glu Ile Phe Leu Leu Gln Glu
210             215                 220 gcc cag gga atg cca cag gta gcc tgg ggg cgt att acg gga gaa aaa     720
Ala Gln Gly Met Pro Gln Val Ala Trp Gly Arg Ile Thr Gly Glu Lys
225             230                 235                 240 gaa tgg aga gat ttg tta agt ctg cat aac gct cag ttt gat ctt ttg     768
Glu Trp Arg Asp Leu Leu Ser Leu His Asn Ala Gln Phe Asp Leu Leu
            245                 250                 255 caa aga act cca gaa gtt gcc cgt agt agg gcc aca cca tta ctc gat     816
Gln Arg Thr Pro Glu Val Ala Arg Ser Arg Ala Thr Pro Leu Leu Asp
        260                 265                 270 atg ata gac act gca tta ttg aca aat ggt aca aca gaa aac agg tat     864
Met Ile Asp Thr Ala Leu Leu Thr Asn Gly Thr Thr Glu Asn Arg Tyr
    275                 280                 285 ggc ata aaa tta ccc gta tct ctg ttg ttt att gct ggt cat gat acc     912
Gly Ile Lys Leu Pro Val Ser Leu Leu Phe Ile Ala Gly His Asp Thr
290             295                 300 aat ctt gca aat tta agc ggg gct tta gat ctt aac tgg tcg cta ccc     960
Asn Leu Ala Asn Leu Ser Gly Ala Leu Asp Leu Asn Trp Ser Leu Pro
305             310                 315                 320 ggt caa ccc gat aat acc cct cct ggt ggg gag ctt gta ttc gaa aag    1008
Gly Gln Pro Asp Asn Thr Pro Pro Gly Gly Glu Leu Val Phe Glu Lys
            325                 330                 335 tgg aaa aga acc agt gat aat acg gat tgg gtt cag gtt tca ttt gtt    1056
Trp Lys Arg Thr Ser Asp Asn Thr Asp Trp Val Gln Val Ser Phe Val
        340                 345                 350 tat cag acg ctg aga gat atg agg gat ata caa ccg ttg tcg tta gaa    1104
Tyr Gln Thr Leu Arg Asp Met Arg Asp Ile Gln Pro Leu Ser Leu Glu
    355                 360                 365 aaa cct gct ggc aaa gtt gat tta aaa tta att gca tgt gaa gag aaa    1152
Lys Pro Ala Gly Lys Val Asp Leu Lys Leu Ile Ala Cys Glu Glu Lys
370             375                 380 aat agt cag gga atg tgt tcg tta aaa agt ttt tcc agg ctc att aag    1200
Asn Ser Gln Gly Met Cys Ser Leu Lys Ser Phe Ser Arg Leu Ile Lys
385             390                 395                 400 gaa att cgc gtg cca gag tgt gca gtt acg gaa                        1233
Glu Ile Arg Val Pro Glu Cys Ala Val Thr Glu
            405                 410

<210> SEQ ID NO 2
<211> LENGTH: 411
<212> TYPE: PRT
<213> ORGANISM: Citrobacter braakii ATCC 51113

<400> SEQUENCE: 2

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65              70                  75                  80

Gly Gln Val Ala Val Ile Ala Asp Thr Asp Gln Arg Thr Arg Lys Thr
            85                  90                  95
```

```
Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Gln Val Lys Asn Ala Ile
        130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 3
<211> LENGTH: 411
<212> TYPE: PRT
<213> ORGANISM: Citrobacter braakii YH-15
<220> FEATURE:
<221> NAME/KEY: mat_peptide
<222> LOCATION: (1)..(411)

<400> SEQUENCE: 3

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
        35                  40                  45
```

Pro Arg Gly Gly Glu Leu Val Ser Glu Leu Gly Gln Tyr Gln Arg Leu
            50                  55                  60

Trp Phe Thr Ser Lys Gly Leu Leu Asn Asn Gln Thr Cys Pro Ser Pro
 65                  70                  75                  80

Gly Gln Val Ala Val Ile Ala Asp Thr Asp Gln Arg Thr Arg Lys Thr
                 85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
                115                 120                 125

Lys Met Gly Lys Cys Ser Phe Asn Thr Leu Lys Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
                180                 185                 190

Leu Pro Ser Glu Phe Lys Val Thr Pro Asp Asn Val Ser Leu Pro Gly
                195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Met Ile Asp Thr Ala Leu Leu Thr Asn Gly Thr Thr Glu Asn Arg Tyr
                275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
                355                 360                 365

Lys Pro Ala Gly Lys Val Asp Leu Lys Leu Ile Ala Cys Glu Glu Lys
                370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 4
<211> LENGTH: 411
<212> TYPE: PRT
<213> ORGANISM: Citrobacter freundii
<220> FEATURE:
<221> NAME/KEY: mat_peptide
<222> LOCATION: (1)..(411)

<400> SEQUENCE: 4

```
Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Thr Asp Pro Leu Phe Asn Pro Val
        115                 120                 125

Lys Met Gly Thr Cys Ser Phe Asn Thr Leu Lys Val Lys Asn Ala Ile
    130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
    210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410
```

<210> SEQ ID NO 5
<211> LENGTH: 1236
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1233)
<220> FEATURE:
<221> NAME/KEY: mat_peptide
<222> LOCATION: (1)..(1233)

<400> SEQUENCE: 5

| | | | | | | | | | | | | | | | | |
|---|---|---|---|---|---|---|---|---|---|---|---|---|---|---|---|---|
| gaa | gag | cag | aat | ggt | atg | aaa | ctt | gag | cgg | gtt | gtg | ata | gtg | agt | cgt | 48 |
| Glu | Glu | Gln | Asn | Gly | Met | Lys | Leu | Glu | Arg | Val | Val | Ile | Val | Ser | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cat | ggr | gta | aga | gca | cct | acg | aag | ttc | act | cca | ata | atg | aaa | aat | gtc | 96 |
| His | Xaa | Val | Arg | Ala | Pro | Thr | Lys | Phe | Thr | Pro | Ile | Met | Lys | Asn | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| aca | ccc | gat | caa | tgg | cca | caa | tgg | gat | gtg | ccg | tta | gga | tgg | cta | acg | 144 |
| Thr | Pro | Asp | Gln | Trp | Pro | Gln | Trp | Asp | Val | Pro | Leu | Gly | Trp | Leu | Thr | |
| | | | 35 | | | | | 40 | | | | | 45 | | | |

| | | | | | | | | | | | | | | | | |
|---|---|---|---|---|---|---|---|---|---|---|---|---|---|---|---|---|
| cct | cgt | ggg | gga | gaa | ctt | gtt | tct | gaa | tta | ggt | cag | tat | caa | cgt | tta | 192 |
| Pro | Arg | Gly | Gly | Glu | Leu | Val | Ser | Glu | Leu | Gly | Gln | Tyr | Gln | Arg | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| tgg | ttc | acg | agc | aaa | ggt | ctg | ttg | aat | aat | caa | acg | tgc | cca | tct | cca | 240 |
| Trp | Phe | Thr | Ser | Lys | Gly | Leu | Leu | Asn | Asn | Gln | Thr | Cys | Pro | Ser | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggg | cag | gtt | gct | gtt | att | gca | gac | acg | gat | caa | cgc | acc | cgt | aaa | acg | 288 |
| Gly | Gln | Val | Ala | Val | Ile | Ala | Asp | Thr | Asp | Gln | Arg | Thr | Arg | Lys | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | gag | gcg | ttt | ctg | gct | ggg | tta | gca | cca | aaa | tgt | caa | att | caa | gtg | 336 |
| Gly | Glu | Ala | Phe | Leu | Ala | Gly | Leu | Ala | Pro | Lys | Cys | Gln | Ile | Gln | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| cat | tat | cag | aag | gat | gaa | gaa | aaa | aat | gat | cct | ctt | ttt | aat | ccg | gta | 384 |
| His | Tyr | Gln | Lys | Asp | Glu | Glu | Lys | Asn | Asp | Pro | Leu | Phe | Asn | Pro | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| aaa | atg | ggg | aaa | tgt | tcg | ttt | aac | aca | ttg | cag | gtt | aaa | aac | gct | att | 432 |
| Lys | Met | Gly | Lys | Cys | Ser | Phe | Asn | Thr | Leu | Gln | Val | Lys | Asn | Ala | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| ctg | gaa | cgg | gcc | gga | gga | aat | att | gaa | ctg | tat | acc | caa | cgc | tat | caa | 480 |
| Leu | Glu | Arg | Ala | Gly | Gly | Asn | Ile | Glu | Leu | Tyr | Thr | Gln | Arg | Tyr | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tct | tca | ttt | cgg | acc | ctg | gaa | aat | gtt | tta | aat | ttc | tca | caa | tcg | gag | 528 |
| Ser | Ser | Phe | Arg | Thr | Leu | Glu | Asn | Val | Leu | Asn | Phe | Ser | Gln | Ser | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| aca | tgt | aag | act | aca | gaa | aag | tct | acg | aaa | tgc | aca | tta | cca | gag | gct | 576 |
| Thr | Cys | Lys | Thr | Thr | Glu | Lys | Ser | Thr | Lys | Cys | Thr | Leu | Pro | Glu | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| tta | ccg | tct | gaa | ctt | aag | gta | act | cct | gac | aat | gta | tca | tta | cct | ggt | 624 |
| Leu | Pro | Ser | Glu | Leu | Lys | Val | Thr | Pro | Asp | Asn | Val | Ser | Leu | Pro | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| gcc | tgg | agt | ctt | tct | tcc | acg | ctg | act | gag | ata | ttt | ctg | ttg | caa | gag | 672 |
| Ala | Trp | Ser | Leu | Ser | Ser | Thr | Leu | Thr | Glu | Ile | Phe | Leu | Leu | Gln | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| gcc | cag | gga | atg | cca | cag | gta | gcc | tgg | ggg | cgt | att | acg | gga | gaa | aaa | 720 |
| Ala | Gln | Gly | Met | Pro | Gln | Val | Ala | Trp | Gly | Arg | Ile | Thr | Gly | Glu | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gaa | tgg | aga | gat | ttg | tta | agt | ctg | cat | aac | gct | cag | ttt | gat | ctt | ttg | 768 |
| Glu | Trp | Arg | Asp | Leu | Leu | Ser | Leu | His | Asn | Ala | Gln | Phe | Asp | Leu | Leu | |
| | | | | 245 | | | | | 250 | | | | | 255 | | |

| | | |
|---|---|---|
| caa aga act cca gaa gtt gcc cgt agt agg gcc aca cca tta ctc gat<br>Gln Arg Thr Pro Glu Val Ala Arg Ser Arg Ala Thr Pro Leu Leu Asp<br>260 265 270 | 816 | |
| atg ata gac act gca tta ttg aca aat ggt aca aca gaa aac agg tat<br>Met Ile Asp Thr Ala Leu Leu Thr Asn Gly Thr Thr Glu Asn Arg Tyr<br>275 280 285 | 864 | |
| ggc ata aaa tta ccc gta tct ctg ttg ttt att gct ggt cat gat acc<br>Gly Ile Lys Leu Pro Val Ser Leu Leu Phe Ile Ala Gly His Asp Thr<br>290 295 300 | 912 | |
| aat ctt gca aat tta agc ggg gct tta gat ctt aac tgg tcg cta ccc<br>Asn Leu Ala Asn Leu Ser Gly Ala Leu Asp Leu Asn Trp Ser Leu Pro<br>305 310 315 320 | 960 | |
| ggt caa ccs gat aay acc ccg ccg ggc gac aag ctt gta ttc gaa aag<br>Gly Gln Xaa Asp Asn Thr Pro Pro Gly Asp Lys Leu Val Phe Glu Lys<br>325 330 335 | 1008 | |
| tgg aaa aga acc agt gat aat acg gat tgg gtt cag gtt tca ttt gtt<br>Trp Lys Arg Thr Ser Asp Asn Thr Asp Trp Val Gln Val Ser Phe Val<br>340 345 350 | 1056 | |
| tat cag acg ctg aga gat atg agg gat ata caa ccg ttg tcg tta gaa<br>Tyr Gln Thr Leu Arg Asp Met Arg Asp Ile Gln Pro Leu Ser Leu Glu<br>355 360 365 | 1104 | |
| aaa cct gct ggc aaa gtt gat tta aaa tta att gca tgt gaa gag aaa<br>Lys Pro Ala Gly Lys Val Asp Leu Lys Leu Ile Ala Cys Glu Glu Lys<br>370 375 380 | 1152 | |
| aat agt cag gga atg tgt tcg tta aaa agt ttt tcc agg ctc att aag<br>Asn Ser Gln Gly Met Cys Ser Leu Lys Ser Phe Ser Arg Leu Ile Lys<br>385 390 395 400 | 1200 | |
| gaa att cgc gtg cca gag tgt gca gtt acg gaa taa<br>Glu Ile Arg Val Pro Glu Cys Ala Val Thr Glu<br>405 410 | 1236 | |

<210> SEQ ID NO 6
<211> LENGTH: 411
<212> TYPE: PRT
<213> ORGANISM: Artificial sequence
<220> FEATURE:
<221> NAME/KEY: misc_feature
<222> LOCATION: (18)..(18)
<223> OTHER INFORMATION: The 'Xaa' at location 18 stands for Gly.
<220> FEATURE:
<221> NAME/KEY: misc_feature
<222> LOCATION: (323)..(323)
<223> OTHER INFORMATION: The 'Xaa' at location 323 stands for Pro.
<220> FEATURE:
<223> OTHER INFORMATION: Synthetic Construct

<400> SEQUENCE: 6

Glu Glu Gln Asn Gly Met Lys Leu Glu Arg Val Val Ile Val Ser Arg
1               5                   10                  15

His Xaa Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Gln Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
    210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

Gly Gln Xaa Asp Asn Thr Pro Pro Gly Asp Lys Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 7
<211> LENGTH: 66
<212> TYPE: DNA
<213> ORGANISM: Citrobacter braakii ATCC 51113
<220> FEATURE:
<221> NAME/KEY: sig_peptide
<222> LOCATION: (1)..(66)
<220> FEATURE:
<221> NAME/KEY: CDS
<222> LOCATION: (1)..(66)

<400> SEQUENCE: 7 atg agt aca ttc atc att cgt tta tta ttt ttt tct ctc tta tgc ggt    48
Met Ser Thr Phe Ile Ile Arg Leu Leu Phe Phe Ser Leu Leu Cys Gly
1               5                   10                  15 tct ttc tca ata cat gct                                            66
Ser Phe Ser Ile His Ala
            20

-continued

<210> SEQ ID NO 8
<211> LENGTH: 22
<212> TYPE: PRT
<213> ORGANISM: Citrobacter braakii ATCC 51113

<400> SEQUENCE: 8

Met Ser Thr Phe Ile Ile Arg Leu Leu Phe Phe Ser Leu Leu Cys Gly
1               5                   10                  15

Ser Phe Ser Ile His Ala
            20

<210> SEQ ID NO 9
<211> LENGTH: 433
<212> TYPE: PRT
<213> ORGANISM: Citrobacter freundii NCIMB 41247
<220> FEATURE:
<221> NAME/KEY: mat_peptide
<222> LOCATION: (1)..(433)

<400> SEQUENCE: 9

Met Ser Thr Phe Ile Ile Arg Leu Leu Phe Phe Ser Leu Leu Cys Gly
1               5                   10                  15

Ser Phe Ser Ile His Ala Glu Glu Pro Asn Gly Met Lys Leu Glu Arg
            20                  25                  30

Val Val Ile Val Ser Arg His Gly Val Arg Ala Pro Thr Lys Phe Thr
        35                  40                  45

Pro Ile Met Lys Asp Val Thr Pro Asp Gln Trp Pro Gln Trp Asp Val
    50                  55                  60

Pro Leu Gly Trp Leu Thr Pro Arg Gly Gly Glu Leu Val Ser Glu Leu
65                  70                  75                  80

Gly Gln Tyr Gln Arg Leu Trp Phe Thr Ser Lys Gly Leu Leu Asn Asn
                85                  90                  95

Gln Thr Cys Pro Ser Pro Gly Gln Val Ala Val Ile Ala Asp Thr Asp
            100                 105                 110

Gln Arg Thr Arg Lys Thr Gly Glu Ala Phe Leu Ala Gly Leu Ala Pro
        115                 120                 125

Lys Cys Gln Ile Gln Val His Tyr Gln Lys Asp Glu Glu Lys Thr Asp
    130                 135                 140

Pro Leu Phe Asn Pro Val Lys Met Gly Thr Cys Ser Phe Asn Thr Leu
145                 150                 155                 160

Lys Val Lys Asn Ala Ile Leu Glu Arg Ala Gly Gly Asn Ile Glu Leu
                165                 170                 175

Tyr Thr Gln Arg Tyr Gln Ser Ser Phe Arg Thr Leu Glu Asn Val Leu
            180                 185                 190

Asn Phe Ser Gln Ser Glu Thr Cys Lys Thr Thr Glu Lys Ser Thr Lys
        195                 200                 205

Cys Thr Leu Pro Glu Ala Leu Pro Ser Glu Leu Lys Val Thr Pro Asp
    210                 215                 220

Asn Val Ser Leu Pro Gly Ala Trp Ser Leu Ser Ser Thr Leu Thr Glu
225                 230                 235                 240

Ile Phe Leu Leu Gln Glu Ala Gln Gly Met Pro Gln Val Ala Trp Gly
                245                 250                 255

Arg Ile Thr Gly Glu Lys Glu Trp Arg Asp Leu Leu Ser Leu His Asn
            260                 265                 270

Ala Gln Phe Asp Leu Leu Gln Arg Thr Pro Glu Val Ala Arg Ser Arg
        275                 280                 285

```
Ala Thr Pro Leu Leu Asp Met Ile Asp Thr Ala Leu Thr Asn Gly
    290                 295                 300

Thr Thr Glu Asn Arg Tyr Gly Ile Lys Leu Pro Val Ser Leu Leu Phe
305                 310                 315                 320

Ile Ala Gly His Asp Thr Asn Leu Ala Asn Leu Ser Gly Ala Leu Asp
                325                 330                 335

Leu Asn Trp Ser Leu Pro Gly Gln Pro Asp Asn Thr Pro Pro Gly Gly
            340                 345                 350

Glu Leu Val Phe Glu Lys Trp Lys Arg Thr Ser Asp Asn Thr Asp Trp
        355                 360                 365

Val Gln Val Ser Phe Val Tyr Gln Thr Leu Arg Asp Met Arg Asp Ile
    370                 375                 380

Gln Pro Leu Ser Leu Glu Lys Pro Ala Gly Lys Val Asp Leu Lys Leu
385                 390                 395                 400

Ile Ala Cys Glu Glu Lys Asn Ser Gln Gly Met Cys Ser Leu Lys Ser
                405                 410                 415

Phe Ser Arg Leu Ile Lys Glu Ile Arg Val Pro Glu Cys Ala Val Thr
            420                 425                 430

Glu

<210> SEQ ID NO 10
<211> LENGTH: 11
<212> TYPE: PRT
<213> ORGANISM: Artificial Sequence
<220> FEATURE:
<223> OTHER INFORMATION: Synthetic construct

<400> SEQUENCE: 10

His Gln Glu Lys Met Gly Thr Met Asp Pro Thr
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic construct

<400> SEQUENCE: 11

His Gln Gln Asp Ile Lys Gln Val Asp Ser Leu
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic construct

<400> SEQUENCE: 12

His Gln Pro Glu Ile Gly Lys Met Asp Pro Val
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic construct
```

```
<400> SEQUENCE: 13

Thr Gln Ala Asp Thr Ser Ser Pro Asp Pro Leu
1               5                   10

<210> SEQ ID NO 14
<211> LENGTH: 11
<212> TYPE: PRT
<213> ORGANISM: Artificial sequence
<220> FEATURE:
<223> OTHER INFORMATION: Synthetic construct

<400> SEQUENCE: 14

His Gln Gln Asp Ile Lys Gln Ala Asp Pro Leu
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic construct

<400> SEQUENCE: 15

Thr Gln Thr Asp Thr Ser Ser Pro Asp Pro Leu
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic construct

<400> SEQUENCE: 16

Asn Gln Ala Asp Leu Lys Lys Thr Asp Pro Leu
1               5                   10

<210> SEQ ID NO 17
<211> LENGTH: 5
<212> TYPE: PRT
<213> ORGANISM: Artificial sequence
<220> FEATURE:
<223> OTHER INFORMATION: Synthetic construct

<400> SEQUENCE: 17

Gln Ala Asp Lys Pro
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic construct

<400> SEQUENCE: 18

Gly Glu Asp Lys Pro
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic construct
```

```
<400> SEQUENCE: 19

Asn Gly Ile Ser Ala
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic construct

<400> SEQUENCE: 20

Ile Ala Gly Lys Ser
1               5

<210> SEQ ID NO 21
<211> LENGTH: 5
<212> TYPE: PRT
<213> ORGANISM: Artificial sequence
<220> FEATURE:
<223> OTHER INFORMATION: Synthetic construct

<400> SEQUENCE: 21

Lys Glu Lys His Gln
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic construct

<400> SEQUENCE: 22

Lys Glu Lys Gln Gln
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic construct

<400> SEQUENCE: 23

Lys Glu Lys Lys Val
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic construct

<400> SEQUENCE: 24

Lys Thr Asp Lys Leu
1               5

<210> SEQ ID NO 25
<211> LENGTH: 30
<212> TYPE: PRT
<213> ORGANISM: Artificial sequence
<220> FEATURE:
<223> OTHER INFORMATION: Synthetic construct
```

```
<400> SEQUENCE: 25

Ala Ala Leu Asn Asn Ser Ile Gly Val Leu Gly Val Ala Pro Ser Ala
1               5                   10                  15

Glu Leu Tyr Ala Val Lys Val Leu Gly Ala Ser Gly Ser Gly
            20                  25                  30

<210> SEQ ID NO 26
<211> LENGTH: 30
<212> TYPE: PRT
<213> ORGANISM: Artificial sequence
<220> FEATURE:
<223> OTHER INFORMATION: Synthetic construct

<400> SEQUENCE: 26

Ala Ala Leu Asn Asn Ser Ile Ala Val Leu Gly Val Ala Pro Ser Ala
1               5                   10                  15

Glu Leu Tyr Ala Val Lys Val Leu Gly Ala Ser Gly Ser Gly
            20                  25                  30

<210> SEQ ID NO 27
<211> LENGTH: 28
<212> TYPE: PRT
<213> ORGANISM: Artificial sequence
<220> FEATURE:
<223> OTHER INFORMATION: Synthetic construct

<400> SEQUENCE: 27

Ala Ala Leu Asn Asn Ser Ile Gly Val Leu Gly Val Ala Pro Ser Ala
1               5                   10                  15

Glu Leu Tyr Ala Val Lys Val Leu Gly Ala Ser Gly
            20                  25

<210> SEQ ID NO 28
<211> LENGTH: 31
<212> TYPE: PRT
<213> ORGANISM: Artificial sequence
<220> FEATURE:
<223> OTHER INFORMATION: Synthetic construct

<400> SEQUENCE: 28

Ala Ala Leu Asn Asn Ser Ile Gly Thr Tyr Val Leu Gly Val Ala Ser
1               5                   10                  15

Pro Ser Ala Glu Leu Tyr Ala Val Lys Val Leu Gly Ala Ser Gly
            20                  25                  30

<210> SEQ ID NO 29
<211> LENGTH: 30
<212> TYPE: PRT
<213> ORGANISM: Artificial sequence
<220> FEATURE:
<223> OTHER INFORMATION: Synthetic construct

<400> SEQUENCE: 29

Ala Ala Leu Asn Asn Ser Ile Gly Val Leu Gly Val Ala Pro Ser Ala
1               5                   10                  15

Glu Leu Tyr Ala Val Lys Val Leu Gly Ala Ser Gly Ser Gly
            20                  25                  30

<210> SEQ ID NO 30
<211> LENGTH: 29
<212> TYPE: PRT
<213> ORGANISM: Artificial sequence
<220> FEATURE:
<223> OTHER INFORMATION: Synthetic construct
```

```
<400> SEQUENCE: 30

Ala Ala Leu Asn Asn Ser Ile Gly Leu Gly Val Ala Pro Ser Ala Glu
1               5                   10                  15

Leu Tyr Ala Val Lys Val Leu Gly Ala Ser Gly Ser Gly
            20                  25

<210> SEQ ID NO 31
<211> LENGTH: 12
<212> TYPE: PRT
<213> ORGANISM: Artificial sequence
<220> FEATURE:
<223> OTHER INFORMATION: Synthetic construct

<400> SEQUENCE: 31

Ala Gln Ser Val Pro Trp Gly Ile Ser Arg Val Gln
1               5                   10

<210> SEQ ID NO 32
<211> LENGTH: 15
<212> TYPE: PRT
<213> ORGANISM: Artificial sequence
<220> FEATURE:
<223> OTHER INFORMATION: Synthetic construct

<400> SEQUENCE: 32

Ala Thr Gly Ala Gln Ser Val Pro Trp Gly Ile Ser Arg Val Gln
1               5                   10                  15

<210> SEQ ID NO 33
<211> LENGTH: 22
<212> TYPE: PRT
<213> ORGANISM: Artificial sequence
<220> FEATURE:
<223> OTHER INFORMATION: Synthetic construct

<400> SEQUENCE: 33

Ala Thr Ser Leu Gly Ser Thr Asn Leu Tyr Gly Ser Gly Leu Val Asn
1               5                   10                  15

Ala Glu Ala Ala Thr Arg
            20

<210> SEQ ID NO 34
<211> LENGTH: 24
<212> TYPE: PRT
<213> ORGANISM: Artificial sequence
<220> FEATURE:
<223> OTHER INFORMATION: Synthetic construct

<400> SEQUENCE: 34

Ala Thr Ser Leu Gly Ser Thr Asn Leu Tyr Gly Ser Gly Leu Val Asn
1               5                   10                  15

Ala Glu Ala Ala Thr Arg Ser Thr
            20
```